US009933609B2

(12) United States Patent
Croquette et al.

(10) Patent No.: US 9,933,609 B2
(45) Date of Patent: Apr. 3, 2018

(54) OPTICAL DEVICE FOR MEASURING THE POSITION OF AN OBJECT

(71) Applicants: Paris Sciences Et Lettres—Quartier Latin, Paris (FR); Centre National de la Recherche Scientifique (CNRS), Paris (FR); Universite Pierre Et Marie Curie (Paris 6), Paris (FR); Universite Paris Diderot Paris 7, Paris (FR)

(72) Inventors: Vincent Croquette, Antony (FR); Jean-François Allemand, Bourg la Reine (FR); Thibault Vieille, Paris (FR)

(73) Assignees: Paris Sciences Et Lettres—Quartier Latin (FR); Centre National de la Recherche Scientifique (CNRS) (FR); Universite Pierre Et Marie Curie (Paris 6) (FR); Universite Paris Diderot Paris 7 (FR)

( * ) Notice: Subject to any disclaimer, the term of this patent is extended or adjusted under 35 U.S.C. 154(b) by 0 days.

(21) Appl. No.: 15/381,320

(22) Filed: Dec. 16, 2016

(65) Prior Publication Data
US 2017/0176735 A1    Jun. 22, 2017

(30) Foreign Application Priority Data
Dec. 18, 2015    (EP) .................................... 15307065

(51) Int. Cl.
G02B 21/36    (2006.01)
G06T 7/70    (2017.01)
(Continued)

(52) U.S. Cl.
CPC ......... *G02B 21/365* (2013.01); *C12Q 1/6816* (2013.01); *G01B 11/002* (2013.01);
(Continued)

(58) Field of Classification Search
CPC ........ H04N 5/33; H04N 5/2256; H04N 5/332; H04N 13/0214; G02B 27/2214; G02B 21/0032; G02B 21/0044; G02B 27/283
See application file for complete search history.

(56) References Cited

U.S. PATENT DOCUMENTS

2002/0102595 A1* 8/2002 Davis .................. C12Q 1/6869
435/6.12
2003/0027187 A1 2/2003 Strick et al.
(Continued)

OTHER PUBLICATIONS

European Search Report for Application No. EP15307065 dated Jun. 10, 2016.
(Continued)

*Primary Examiner* — Hung Dang
*Assistant Examiner* — Sunghyoun Park
(74) *Attorney, Agent, or Firm* — Lerner, David, Littenberg, Krumholz & Mentlik, LLP

(57) ABSTRACT

The invention relates to an optical device for measuring the position of an object along a first axis, the object being subjected to light radiations emitted by a light source. The optical device comprises: an imaging system comprising an objective for collecting light radiations diffused by the object, the imaging system having an optical axis extending parallel to the first axis; a transmission mask having at least a first aperture and a second aperture, the first aperture and second aperture being spaced from each other along a second axis, perpendicular to the first axis, the transmission mask being arranged so as to let a first part of the radiations and a second part of the radiations which are diffused by the object pass through the first aperture and the second aperture respectively, while blocking a part of the radiations emitted by the light source which is not diffused by the object; and a detector adapted for generating an image including a first spot and a second spot representative of the first part and
(Continued)

second part of the radiations impacting the detector plane, wherein variation of the position of the object relative to the object plane of the imaging system along the first axis causes variation of a position of the first spot and of the second spot relative to each other along the second axis.

21 Claims, 27 Drawing Sheets

(51) Int. Cl.
| | | |
|---|---|---|
| G02B 5/00 | (2006.01) | |
| G02B 5/04 | (2006.01) | |
| G02B 21/02 | (2006.01) | |
| G02B 21/08 | (2006.01) | |
| G02B 21/18 | (2006.01) | |
| G02B 21/24 | (2006.01) | |
| H04N 5/225 | (2006.01) | |
| C12Q 1/68 | (2018.01) | |
| G01B 11/00 | (2006.01) | |
| G02B 21/00 | (2006.01) | |
| G02B 21/10 | (2006.01) | |

(52) U.S. Cl.
CPC ............... *G02B 5/005* (2013.01); *G02B 5/04* (2013.01); *G02B 21/0032* (2013.01); *G02B 21/0052* (2013.01); *G02B 21/02* (2013.01); *G02B 21/086* (2013.01); *G02B 21/10* (2013.01); *G02B 21/18* (2013.01); *G02B 21/241* (2013.01); *G02B 21/361* (2013.01); *G06T 7/70* (2017.01); *H04N 5/2256* (2013.01)

(56) References Cited

U.S. PATENT DOCUMENTS

| | | | |
|---|---|---|---|
| 2007/0183943 A1* | 8/2007 | Golovkina | B01J 19/0046 422/186.3 |
| 2008/0278804 A1 | 11/2008 | Gharib et al. | |
| 2011/0254928 A1* | 10/2011 | Meinherz | G01B 11/22 348/46 |
| 2012/0281113 A1* | 11/2012 | Kennedy | H01L 27/14618 348/231.6 |
| 2013/0136311 A1 | 5/2013 | Nishizaka et al. | |
| 2014/0293037 A1* | 10/2014 | Kleppe | G02B 21/0032 348/80 |

OTHER PUBLICATIONS

Michael P. Lee et al: "Spatial light modulation for improved microscope stereo vision and 3D tracking", Optical Sensing II, vol. 8810, Sep. 12, 2013, p. 881022, XP055279790.

Richard Bowman et al: "Particle tracking stereomicroscopy in optical tweezers: Control of trap shape", Optics Express, vol. 18, No. 11, May 24, 2010, p. 11785, XP055279760.

* cited by examiner

Bottom fringes

Top fringes

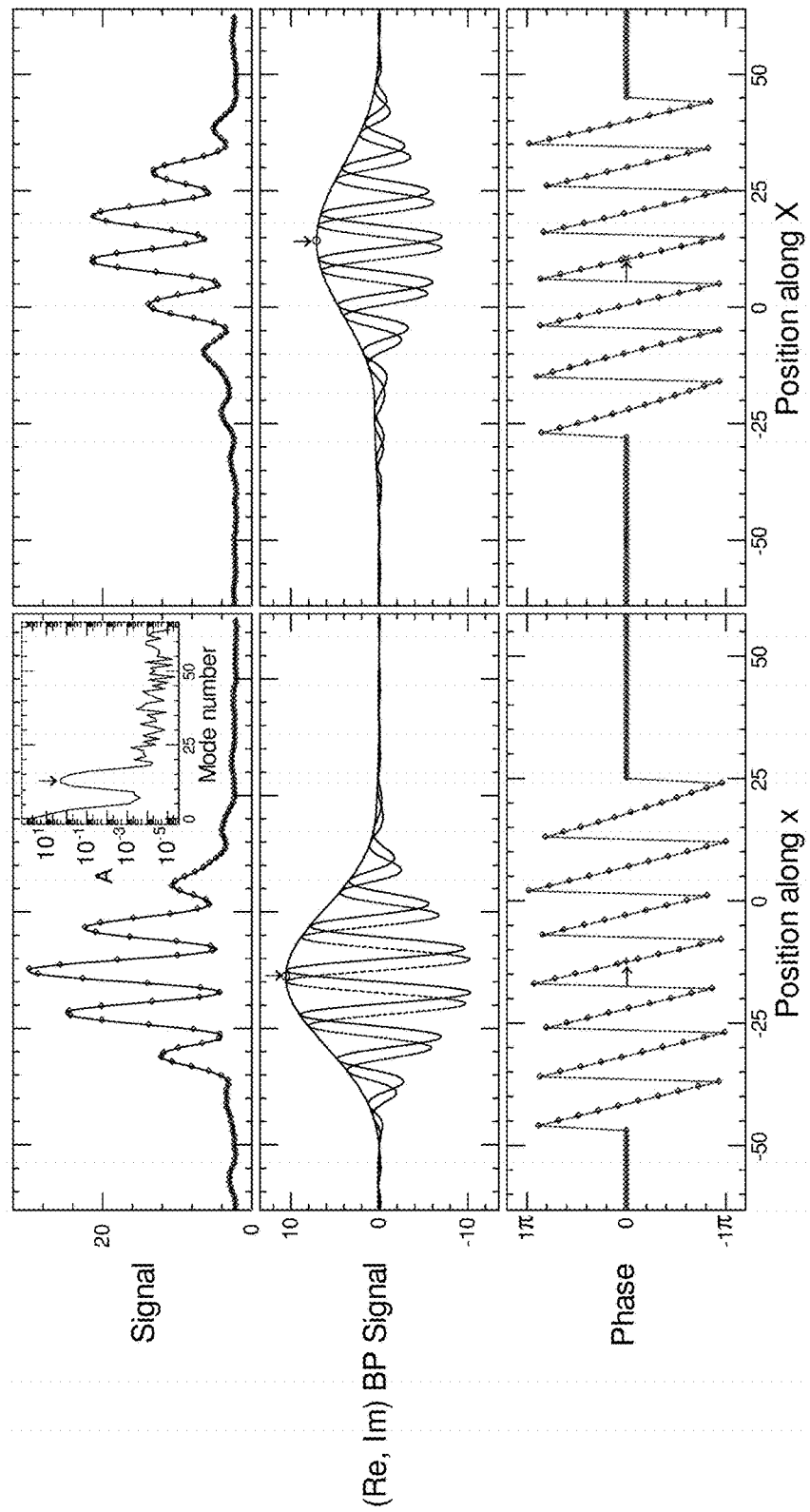

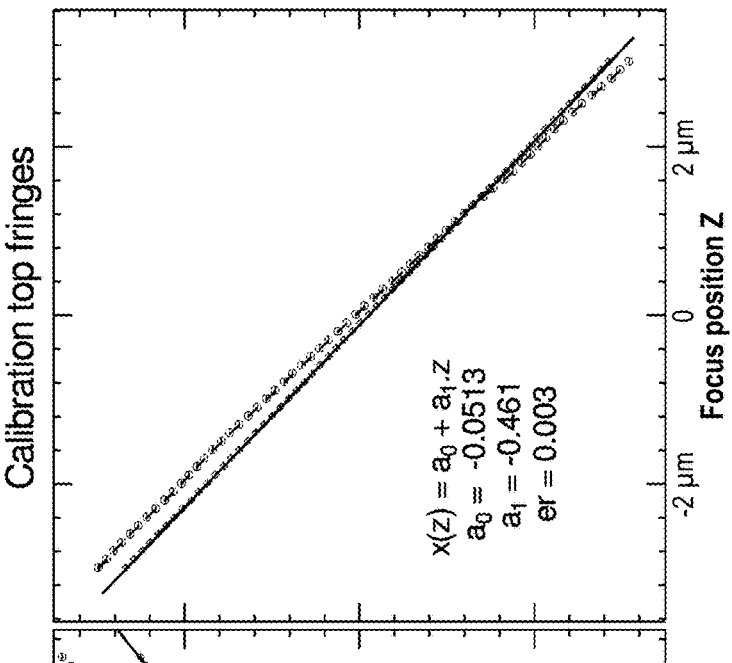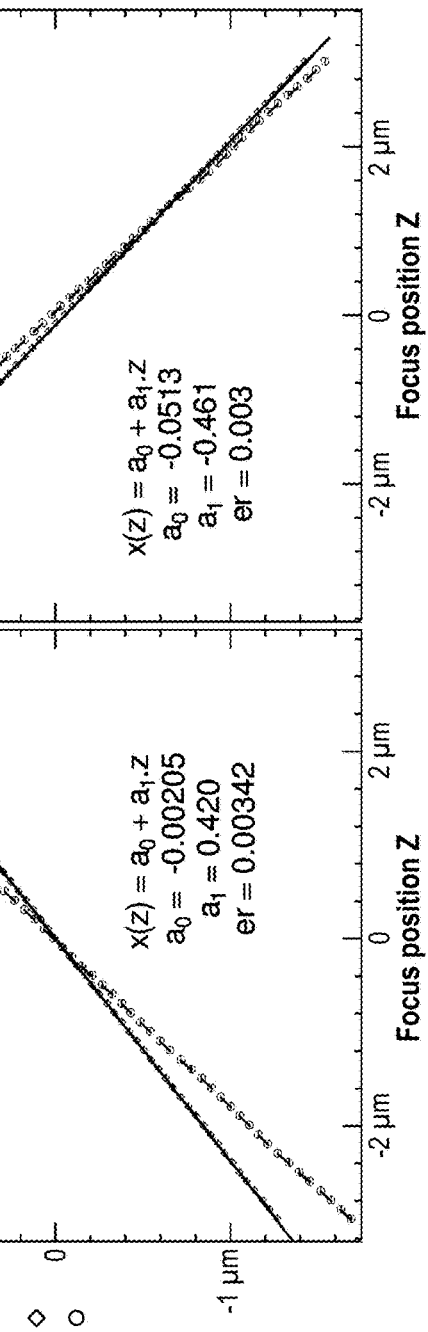
FIG. 20B
FIG. 20A

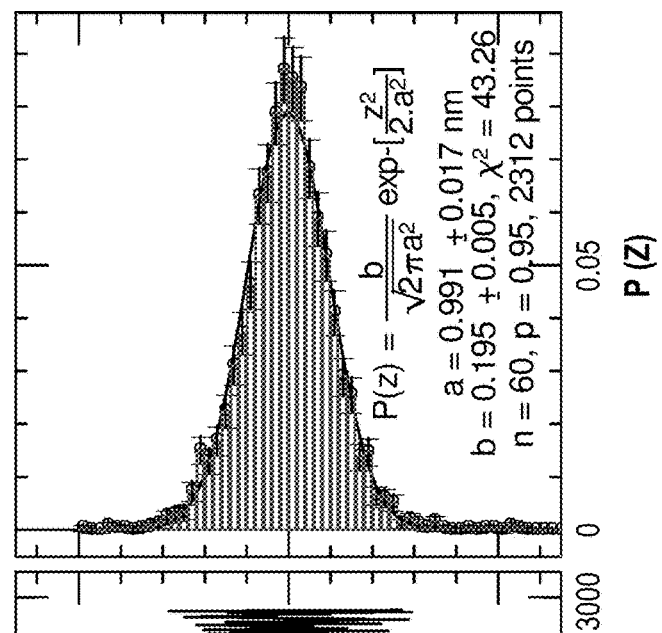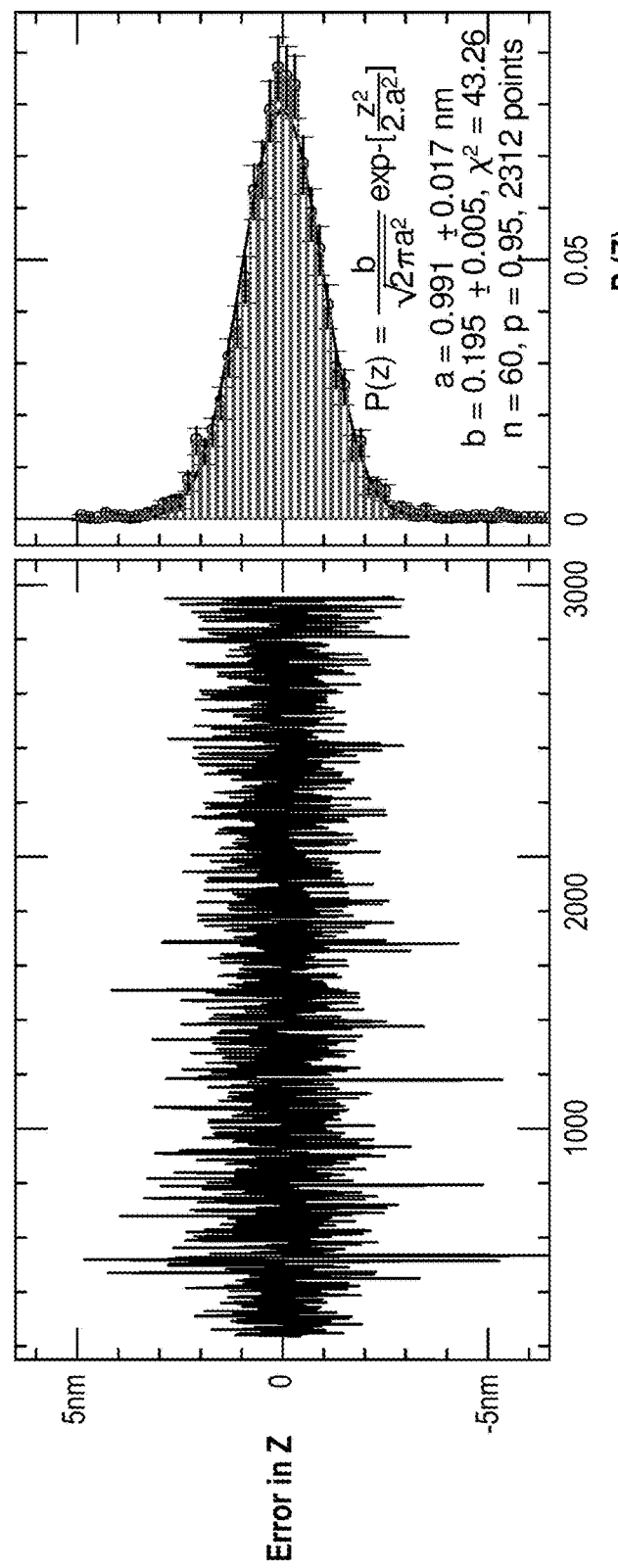

OPTICAL DEVICE FOR MEASURING THE
POSITION OF AN OBJECT

CROSS REFERENCE TO RELATED
APPLICATION

This application claims the benefit of the filing date of European Patent Application Serial No. 15307065.1, filed Dec. 18, 2015, the disclosure of which is incorporated herein by reference.

TECHNICAL FIELD OF THE INVENTION

The present invention relates to an optical device for measuring the position of one or several objects. The invention finds particular application for measuring positions of quasi-punctual objects, such as microbeads, with a high precision.

BACKGROUND ART

In order to study interactions between DNA molecules and other components, such as proteins, it is known to submit the DNA molecules to stretching forces and to measure the elastic properties (i.e. relative extension versus force characteristics) of the molecules.

Document US 2003/0027187 discloses for instance an apparatus for testing a DNA molecule wherein the molecule is anchored at one end to an anchoring surface and at the other end to a paramagnetic bead. The apparatus comprises magnets for applying a force to the bead so as to control the stretching and torsion of the molecule. The apparatus also comprises a light source, a microscope and a camera for generating an image of the bead, as well as a computer for analyzing the image generated.

Analysis of the image of the bead allows determining in real time the position of the bead in three dimensions (x, y, z), and thus the extension of the molecule and the applied stretching force.

The x, y coordinates of the bead may be determined by using the symmetry of the bead and determining its center by auto-convolution. Indeed, this function presents a maximum positive value which position is shifted by (2δx, 2δy) where δx(δy) is the shift of the bead image along x(y) from the original image center. Auto-convolution may be computed rapidly using a FFT algorithm and the maximum position may be obtained by locally fitting a second order polynomial.

The z coordinate of the bead (i.e. coordinate of the bead along the magnification axis of the microscope) may be determined by comparing the diffraction pattern of the bead to a set of reference diffraction patterns previously acquired during a calibration phase.

Indeed, interferences between light radiations emitted by the light source and light radiations diffused by the bead generate diffraction rings in the image recorded by the camera. The size of the diffraction rings varies with the distance of the bead relative to the focal plane of the microscope.

Calibration of the apparatus consists in recording several images of the bead by varying focusing of the microscope while keeping the bead in a fixed position relative to the anchoring surface. This calibration phase allows generation of different reference images of the bead corresponding to different distances between the bead and the focus plane.

Once the calibration phase has been completed, comparison of the current image of the bead with the reference images, allows measurement of the position of the bead with a precision of few nanometers. For instance, the method allows following positions of a few dozen of beads, with a precision of about 3 nanometers between two video images. In applications wherein the apparatus is used for measuring the length of the DNA molecule, this allows localizing a sequence component of the DNA molecule to within few nucleobases.

However, the calibration phase is time consuming, requires large computing resources and must be carried out for each bead separately.

Moreover, the proposed method requires the use of a large number of pixels on the camera used to image one bead, especially if one wishes to test long DNA molecules because of the increasing of the size of the image of the object. This may limit the number of beads one is able to analyze (for instance 1000 beads for a 4 megapixels camera).

Therefore, the proposed method may not be extended for simultaneously measuring positions of a large number of beads, such as thousands of beads for instance.

In addition, in order to vary focusing of the microscope, the calibration phase requires the use of a high precision nano-positioning stage, including piezoelectric actuators, for moving the anchoring surface relative to the microscope in a precise and repeatable way.

SUMMARY OF THE INVENTION

One aim of the invention is to provide an optical device for measuring a position of an object with a high precision, which does not necessitate a calibration phase.

According to a first aspect, the invention provides an optical device for measuring the position of an object along a first axis, the object being subjected to light radiations emitted by a light source, the optical device comprising:
  an imaging system comprising an objective for collecting light radiations diffused by the object, the objective having an optical axis extending parallel to the first axis,
  a transmission mask having at least a first aperture and a second aperture, the first aperture and second aperture being spaced from each other along a second axis, perpendicular to the first axis, the transmission mask being arranged so as to let a first part of the radiations and a second part of the radiations which are diffused by the object pass through the first aperture and the second aperture respectively, while blocking a part of the radiations emitted by the light source which is not diffused by the object,
  a separating arrangement for separating the first part of the radiations from the second part of the radiations in opposite directions along a third axis, perpendicular to the first and second axes, and
  a detector having a detector plane, the detector being adapted for generating an image including a first spot and a second spot, the first spot and the second spot being representative of the separated first part and second part of the radiations impacting the detector plane,
  wherein variation of the position of the object relative to an object plane of the imaging system along the first axis causes variation of a position of the first spot and of the second spot relative to each other along the second axis.

In such an optical device, the transmission mask allows selecting two radiation parts from the light radiations diffused by the object so as to generate two spots in the image recorded by the detector. As the distance between the two spots along the second axis is proportional to the distance between the bead and the object plane of the imaging system, it is possible to infer, from the image, the position of the bead according to the first axis.

In addition, the transmission mask blocks the part of the radiations coming directly from the source. Therefore, radiations coming directly from the source do not reach the objective so that only radiations which have been diffused (i.e. deviated) by the object may be observed in the image generated by the detector. This greatly improves the contrast of the image and therefore increases the precision of the measurements.

The separating arrangement spatially shifts the two radiation parts apart from each other along the third axis. This prevents overlapping of the two spots when the two radiation parts cross each other in the plane of the detector.

Moreover, as the two spots are shifted along the third axis, it is possible to determine whether the two radiation parts cross each other before or after the detector plane so as to discriminate between positive and negative values of the position of the image plane of the bead relative to the detector plane.

In addition, the optical device may have the following features:
- according to a first embodiment, the transmission mask comprises only two apertures,
- the first aperture and the second aperture are arranged symmetrically on opposite sides of the first axis,
- the optical device comprises a processing module for processing the image generated by the detector, the processing module being configured for:
  determining a position of a center of the first spot in the image,
  determining a position of a center of the second spot in the image, and
  computing the position of the object along the first axis as a function of the position of the center of the first spot and of the position of the center of the second spot,
  the processing module may be configured for determining the position of the center of each spot by computing a maximum of the auto-convolution of an average profile of the spot,
  the processing module is configured for determining the position of the object along the second axis and/or along the third axis from positions of the spots on the image,
- according to a second embodiment, the transmission mask comprises a first pair of apertures dividing the first part of the radiations into two first beams, and a second pair of apertures dividing the second part of the radiations into two second beams, and wherein the two first beams interfere with each other so as to create a first interference pattern within the first spot and the two second beams interfere with each other so as to create a second interference pattern within the second spot,
- the optical device comprises a processing module for processing the image generated by the detector, the processing module being configured for determining a spatial phase shift between the first interference pattern and the second interference pattern along the second axis, and for determining a position of the object along the first axis as a function of said spatial phase shift, determination of the spatial phase shift may comprise:
  generating a first signature signal representative of a spatial variation of the intensity of the first spot along the second axis,
  generating a second signature signal representative of a spatial variation of the intensity of the second spot along the second axis, and
  determining a first reference point of the first signature signal where a phase of the first signature signal is null near a maximum of an amplitude of the first signature signal determining a second reference point of the second signature signal where a phase of the second signature signal is null near a maximum of an amplitude of the second signature signal,
  computing the spatial phase shift between the first interference pattern and the second interference pattern as the distance along the second axis between the first point and the second point,
  the processing module may also be configured for determining the position of the object along the second axis from the first reference point and the second reference point,
  the processing module may also be configured for determining the position of the object along the third axis, determination of the position of the object along the third axis comprising:
  generating a third signature signal representative of a spatial variation of the intensity of the first spot and of the second spot along the third axis,
  computing an auto-convolution signal by auto-convolution of the third signature signal,
  determining a maximum of the auto-convolution signal, the coordinate of the maximum of the auto-convolution signal along the third axis y being considered as being twice the position of the bead along the third axis y,
  the optical device may comprise a first light source arranged to emit light radiations toward the object according to a first angle and a second light source arranged to emit light radiations toward the object according to a second angle,
  the first light source and the first pair of apertures may be arranged such that a part of the light radiations emitted by the first light source and diffused by the object passes through the first pair of apertures while a part of the light radiations emitted by the first light source but which is not diffused by the object is blocked by the transmission mask,
  the second light source and the second pair of apertures may be arranged such that a part of the light radiations which is emitted by the second light source and diffused by the object passes through the second pair of apertures while a part of the light radiations emitted by the second light source and which is not diffused by the object is blocked by the transmission mask,
  the light source may be a light source with a short length of coherence (i.e. less than around 100 µm) such as a light emitting diode (LED),
  the separating arrangement may comprise at least one blade having a face which is inclined relative to a plane perpendicular to the first axis, so that the first part or the second part of the light radiations which goes through the blade is translated along the third axis,
  the separating arrangement may comprise at least one prism having a face which is inclined relative to a plane perpendicular to the first axis, so that the first part or the second part of the light radiations which goes through the prism is deviated along the third axis,
  the transmission mask may be located in a Fourier plane of the imaging system or in a plane which is an image of the Fourier plane of the imaging system through an optical relay, so as to select parts of the light radiations which have been diffused by the object according to predetermined angles.

According to a second aspect, the invention provides an optical device for measuring the position of an object along a first axis, the object being subjected to light radiations emitted by a light source, the optical device comprising:

an imaging system comprising an objective for collecting light radiations diffused by the object, the objective having an optical axis extending parallel to the first axis, a transmission mask having at least a first pair of apertures and a second pair of apertures, dividing the radiation diffused by the object into two first beams passing through the first pair of apertures and two second beams passing through the second pair of apertures, while blocking a part of the radiations emitted by the light source which is not diffused by the object, and a detector having a detector plane, the detector being adapted for generating an image including a first spot and a second spot, the first spot and the second spot being representative of the first beams and second beams impacting the detector plane respectively, the two first beams interfering with each other so as to create a first interference pattern within the first spot and the two second beams interfering with each other so as to create a second interference pattern within the second spot.

wherein variation of the position of the object relative to an object plane of the imaging system along the first axis causes spatial phase shifting of first interference patterns and of the second interference pattern relative to each other.

The transmission mask allows selecting two pairs of beams from the light radiations diffused by the object so as to generate two spots having interference pattern in the image recorded by the detector. As the spatial phase shift of the interference patterns relative to each other depends on the distance between the bead and the object plane of the imaging system, it is possible to infer, from the image, the position of the bead according to the first axis with a very high precision. The precision of the measurement depends on the distance between two successive interference fringes in the interferences patterns, and thus in part on the wavelength of the radiations emitted by the source.

In addition, the optical device may have the following features:

the optical device may comprise a processing module for processing the image generated by the detector, the processing module being configured for determining a spatial phase shift between the first interference pattern and the second interference pattern along the second axis, and for determining a position of the object along the first axis as a function of said spatial phase shift, determination of the spatial phase shift may comprise:

generating a first signature signal representative of a spatial variation of the intensity of the first spot along the second axis, generating a second signature signal representative of a spatial variation of the intensity of the second spot along the second axis, and determining a first reference point of the first signature signal where a phase of the first signature signal is null near a maximum of the amplitude of the signal, determining a second reference point of the second signature signal where a phase of the second signature signal is null near a maximum of the amplitude of the signal computing the spatial phase shift between the first interference pattern and the second interference pattern as the distance along the second axis between the first point and the second point, the processing module may be configured for determining the position of the object along the second axis from the first reference point and the second reference point, the processing module may be configured for determining the position of the object along the third axis, determination of the position of the object along the third axis comprising:

generating a third signature signal representative of a spatial variation of the intensity of the first spot and of the second spot along the third axis, computing an auto-convolution signal by auto-convolution of the third signature signal, determining a maximum of the auto-convolution signal, the coordinate of the maximum of the auto-convolution signal along the third axis y being considered as being twice the position of the bead along the third axis y, the optical device may comprise a first light source arranged to emit light radiations toward the object according to a first angle and a second light source arranged to emit light radiations toward the object according to a second angle, the first light source and the first pair of apertures may be arranged such that a part of the light radiations emitted by the first light source and diffused by the object passes through the first pair of apertures while a part of the light radiations emitted by the first light source but which is not diffused by the object is blocked by the transmission mask, the second light source and the second pair of apertures may be arranged such that a part of the light radiations which is emitted by the second light source and diffused by the object passes through the second pair of apertures while a part of the light radiations emitted by the second light source and which is not diffused by the object is blocked by the transmission mask, the light source may be a light source with a short length of coherence (i.e. less than around 100 μm), such as a light emitting diode (LED), the separating arrangement may comprise at least one blade having a face which is inclined relative to a plane perpendicular to the first axis, so that the first part or the second part of the light radiations which goes through the blade is translated along the third axis, the separating arrangement may comprise at least one prism having a face which is inclined relative to a plane perpendicular to the first axis, so that the first part or the second part of the light radiations which goes through the prism is deviated along the third axis, the transmission mask may be located in a Fourier plane of the objective or in a plane which is an image of the Fourier plane of the objective through an optical relay, so as to select parts of the light radiations which have been diffused by the object according to predetermined angles.

The invention also relates to a method for measuring a position of an object using a device as defined previously.

According to an embodiment of the invention, the object may be a magnetic bead.

According to an embodiment of the invention, a molecule having two ends is attached at one end to an anchoring surface and at the other end to the magnetic bead, the device being positioned relative to the anchoring surface so as to measure a distance between the magnetic bead and the anchoring surface.

According to an embodiment of the invention, a plurality of molecules are attached, each molecule being attached at one end to the anchoring surface and at the other end to an associated magnetic bead, and the method comprises a step of generating an image showing a plurality of pairs of spots, each pair of spots being generated by one of the magnetic beads, and scanning the image for determining for each successive pair of spots, a distance between the magnetic bead and the anchoring surface.

Moreover, the maximum size of an image of an object obtained with this invention is smaller than the maximum size of the image in the previous method described in the background art, especially for long travel of the object along the first axis. Thus, one aim of the invention is also to increase the number of objects whose position can be measured by using a lower number of pixels for long travel range.

BRIEF DESCRIPTION OF THE DRAWINGS

The invention will be described with reference to the drawings, in which:

FIGS. 19A and 19B are diagrams showing different signals generated by the processing module when processing the images of the spots: the first signal is a Fourier transform of the averaged interference profile of each spot, the second signal is obtained by band-pass filtering the first signal, and the third signal is the phase signal of the second signal, FIGS. 20A and 20B are diagrams showing the position of the fringes pattern measured using the phase signal (diamonds full lines) or the maximum of amplitude (circle dash lines) for the first spot and for the second spot respectively, FIGS. 21A and 21B are diagrams showing respectively an error signal (that is the value of the signal minus the mean value of each step) and a corresponding distribution of the error signal.

DETAILED DESCRIPTION OF ONE EMBODIMENT OF THE INVENTION

Figure 1:
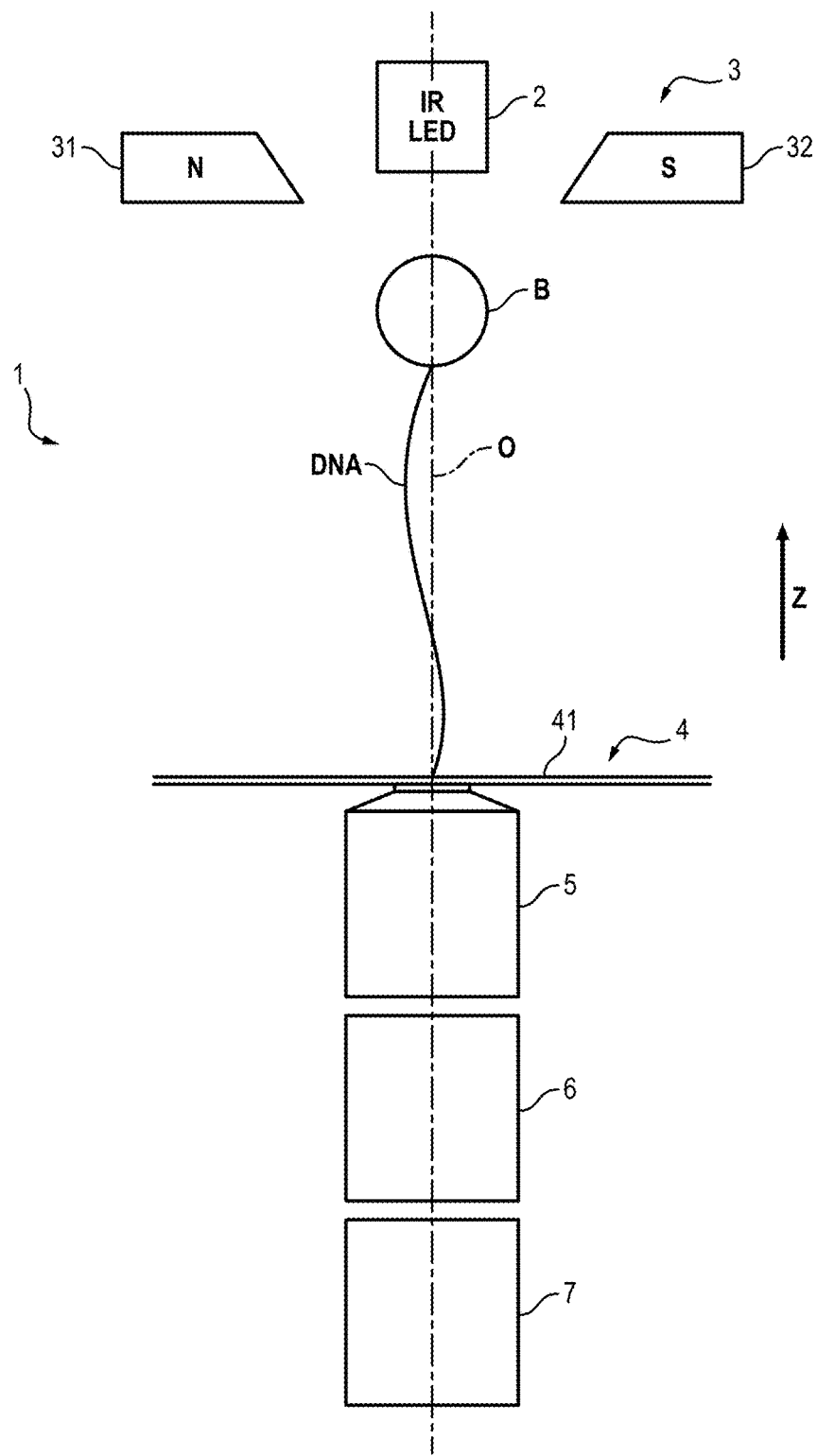
FIG. 1 diagrammatically shows a device used for measuring a position of a bead attached to a DNA molecule, FIG. 2 diagrammatically shows a device according to a first embodiment of the invention, FIG. 3 diagrammatically illustrates two ray paths in the device of FIG. 2, FIG. 4 diagrammatically illustrates two spots generated in the detector plane with the device of FIG. 2, FIGS. 5 and 6 diagrammatically illustrates two different configurations of the spots obtained for two positions of the bead.

In the example illustrated on FIG. 1, the optical device 1 according to the invention is used for detecting the configuration of a molecule, such as a DNA molecule.

In this example, the device 1 comprises a light source 2, a magnetic tweezer 3, a support 4, an optical imaging system 5, a detector 6 and a processing module 7.

The light source 2 comprises a monochromatic light-emitting diode (LED) adapted for emitting light radiations. Different wavelengths may be used depending on the desired accuracy of the device. However, short wavelength may damage the DNA molecule. Therefore, the wavelength of the radiation is preferably comprised between 200 nanometers (frequency 1505 THz) and 1 millimeter (frequency 300 GHz).

The magnetic tweezer 3 comprises two magnets 31 and 32, which may be permanent magnets.

The support 4 is made of a material which is transparent to the light radiations emitted by the light source 2, such as glass for instance. The support 4 has an anchoring surface 41 to which the DNA molecule is attached. The support 4 may be a part of a capillary tube allowing introduction of a liquid solution in which the DNA molecule is immersed. In that case, the anchoring surface 41 is an internal surface of the capillary tube.

As illustrated on FIG. 1, the DNA molecule is attached at one end to a magnetic (paramagnetic or ferromagnetic) bead B and at the other end to the anchoring surface 41. The magnetic bead B may be a polystyrene bead with incorporated ferrite. The magnetic bead B may have a diameter of few micrometers or less. The DNA molecule may be labelled with biotin and digoxigenin at its ends, while the bead B is coated with streptavidin and the anchoring surface 41 is coated with antidigoxigenin antibodies.

The optical imaging system 5 is adapted for collecting light radiations diffused by the bead B. The optical imaging system 5 has a magnification axis, which is also the optical axis O of the optical device 1. The optical axis O is parallel to a first direction z. The anchoring surface 41 extends substantially perpendicularly to the magnification axis O of the optical objective 5.

The two magnets 31 and 32 are arranged at a distance from the anchoring surface 41, on opposite sides of the magnification axis O. The magnets 31, 32 are designed for generating a magnetic field so as to apply a magnetic force on the bead B and consequently a stretching force on the DNA molecule. By moving the magnets 31, 32 closer to or farther from the anchoring surface 41, it is possible to adjust the magnetic field gradient and thus control the stretching force applied to the molecule.

The detector 6 is interposed between the imaging system 5 and the processing module 7. The detector 6 may be a charge-coupled device (CCD) or a complementary metal-oxide-semiconductor (CMOS) camera. The detector 6 is arranged to receive light radiations transmitted by the optical imaging system 5 and to generate a corresponding image.

The processing module 7 may be a PC computer, a processor, an electronic card, a dedicated integrated circuit or a programmable electronic component. The processing module 7 is configured to analyze the image generated by the detector 6 and determine a position of the bead B based on the generated image.

Figure 2:
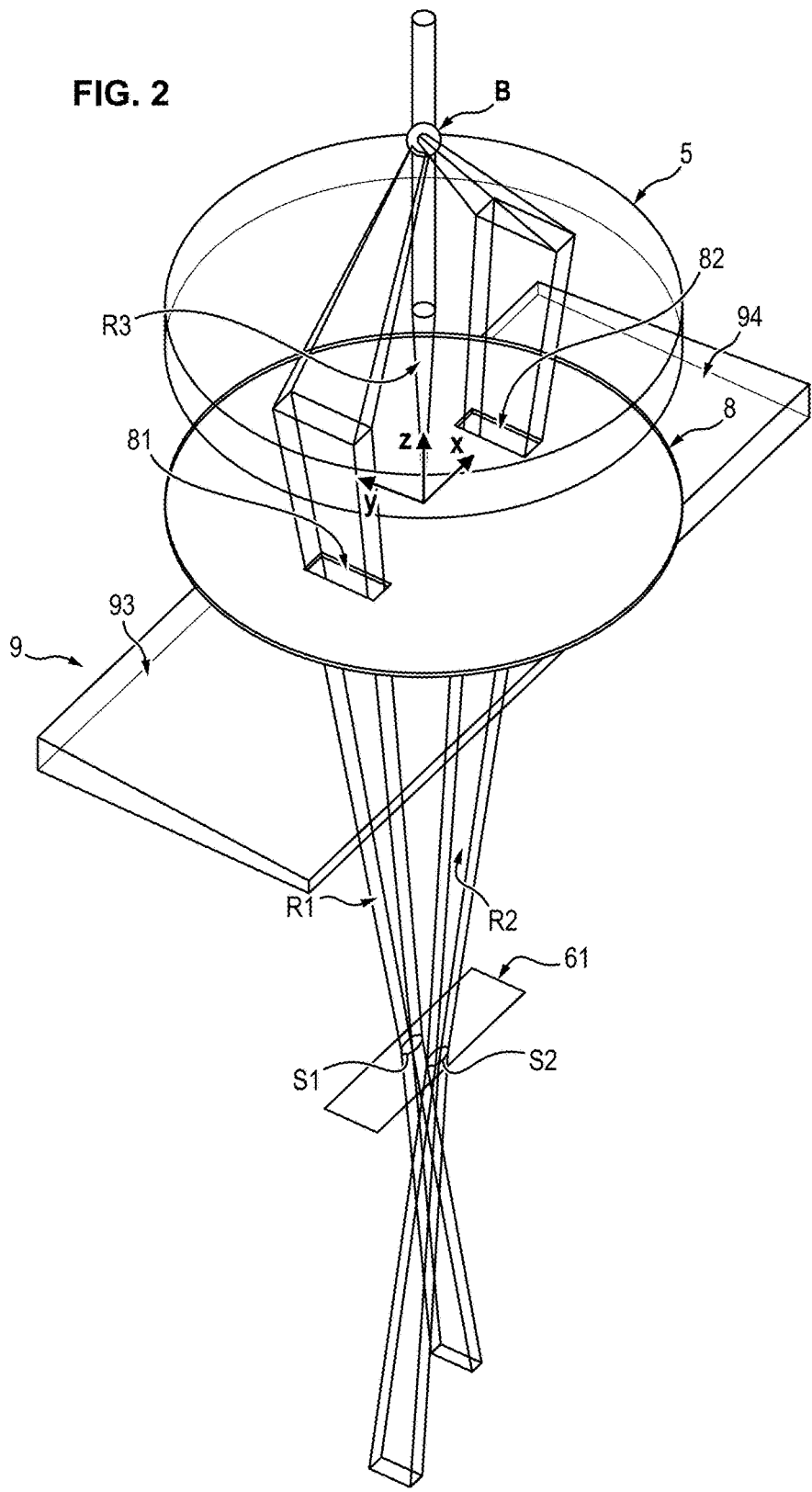

FIG. 2 illustrates a first embodiment of the optical device 1 according to the invention. In this figure, the optical imaging system 5 comprises an optical finite-objective 53 (i.e. an optical objective which is configured to provide an image of an object at a finite distance). On FIG. 2, the optical finite-objective 53 has been represented in a simplified manner, as a single lens.

As illustrated on FIG. 2, the optical device 1 comprises a transmission mask 8 and a separating arrangement 9.

The transmission mask 8 is located in the Fourier plane of the optical objective 53 of the imaging system 5.

The transmission mask 8 has a first aperture 81 and a second aperture 82. In the example illustrated on FIG. 2, the first aperture 81 and second aperture 82 consist of a first slot and a second slot. The slots 81 and 82 are located symmetrically on opposite sides of the optical axis O and are spaced from each other along a second axis x, perpendicular to the first axis z. In addition, both the first slot 81 and second slot 82 have a length which extends parallel to a third axis y, perpendicular to the first axis z and the second axis x.

The transmission mask 8 is arranged so as to let a first part R1 of the radiations emitted by the source 21 and diffused by the bead B pass through the first aperture 81 and a second part R2 of the radiations emitted by the source 21 and diffused by the bead B pass through the second aperture 82. The transmission mask 8 is also arranged to block a third part R3 of the radiations which is directly emitted by the light source 2 (i.e. part of the radiations which has not been diffused by the bead). In other words, the transmission mask is arranged to select two parts R1 and R2 of the radiations diffused by the bead B.

The separating arrangement 9 is arranged for spatially separating the first part R1 of the radiations and the second part R2 of the radiations which have been selected by the amplitude mask 8. The first part R1 and the second part R2 of the radiations are shifted by the separating arrangement 9 in opposite directions along the third axis y, perpendicular to the first and second axes z and x. As a result, the first part R1 of the radiations and the second part R2 of the radiation do not meet with each other. This prevent the first part R1 and the second part R2 of the radiations from interfering with each other.

The separated first part R1 and second part R2 of the radiations impact the plane 61 of the detector 6, generating respectively a first spot S1 and a second spot S2. Due to the presence of the separating arrangement 9, the first spot S1 and the second spot S2 do not overlap, even when the first part R1 and second part R2 of the radiations have the same position along the second axis x in the detector plane 61.

Figure 3:
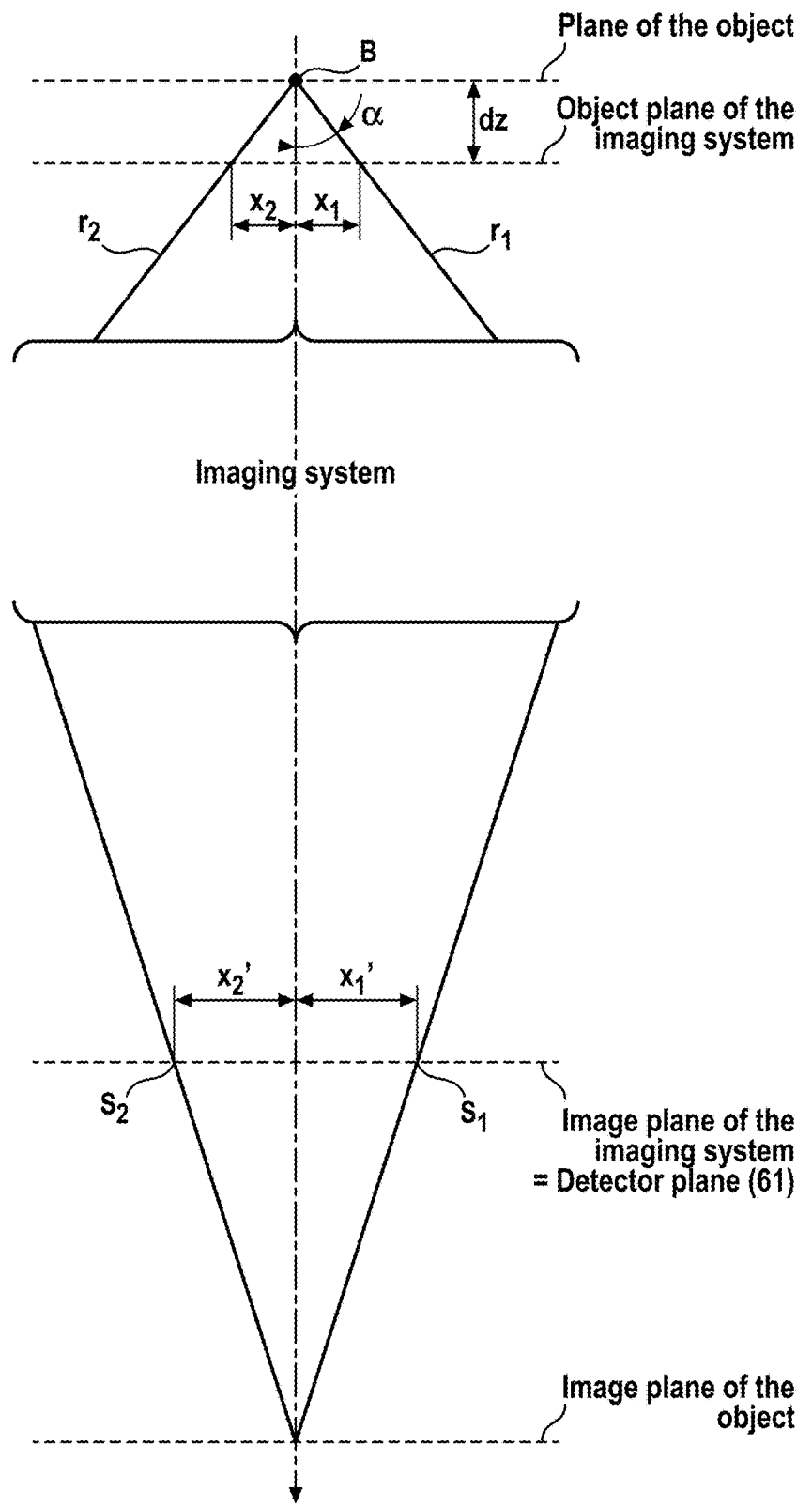

In FIG. 3, the first part R1 and second part R2 of the radiations have been represented in a simplified manner as two individual rays $r_1$ and $r_2$. The first spot S1 and the second spot S2 have also been represented in a simplified manner, as two impact points $s_1$ and $s_2$. As shown on this figure, the transmission mask 8 allows selecting the two rays $r_1$ and $r_2$ according to their respective angles $\alpha$ relative to the optical axis O. Rays $r_1$ and $r_2$ impact the detector plane respectively at two impact points $s_1$ and $s_2$ separated from the optical axis of distances $x'_1$ and $x'_2$ along the second axis x.

The first point $s_1$ and the second point $s_2$ represent two images of the bead, whose coordinate in the detection plane along the second axis x are $x_1'$ and $x_2'$ respectively. The first point $s_1$ and the second point $s_2$ are separated from each other by a distance $x_1'-x_2'$ along the second axis x. As shown on FIG. 3, positions of the impact points $s_1$ and $s_2$ are linked to the distance dz between the bead and the object plane of the imaging system, as follows:

$$x_1 = dz \cdot \tan \alpha$$

$$x_2 = -dz \cdot \tan \alpha$$

where dz is the distance between the bead and the object plane of the imaging system along the first axis z and $\alpha$ is the opening angle for the selected rays $r_1$ and $r_2$.

Thus, since the first point $s_1$ and the second point $s_2$ are in the image plane of the imaging system, their positions $x'_1$ and $x'_2$ in the image plane are given by the following relationships:

$$x'_1 = g_y \cdot x_1$$

$$x'_2 = g_y \cdot x_2$$

where $g_y$ is the lateral magnification of the optical imaging system, and $\alpha$ is the angle of the selected rays relative to the optical axis O.

The distance $x_1'-x_2'$ between the two impact points $s_1$ and $s_2$ of the two rays $r_1$ and $r_2$, in the detector plane is proportional to the position of the bead along the first axis z, and is given by:

$$dz = \frac{1}{2g_y \tan \alpha}(x'_2 - x'_1)$$

where $g_y$ is the lateral magnification of the imaging system, and α is the angle of the selected rays relative to the optical axis O.

The sensitivity of the optical device 1 is therefore proportional to the magnification and to the tangent of the aperture angle of the optical imaging system, while the numerical aperture defined by n sin α defines the maximum possible angles.

At the same time, the position of the bead along the second axis x can be deduced with the following relationship:

$$x = \frac{x'_1 + x'_2}{2g_y}$$

where x is the coordinate of the bead along the second axis x.

If the case that the slots 81 and 82 are not properly centered, leading to different angles, and for a bead which would not be placed on the optical axis O, then the relations would become:

$$x_1 - x = dz \cdot \tan\alpha_1$$

$$x_2 - x = -dz \cdot \tan\alpha_2$$

where $\tan\alpha_1$ and $\tan\alpha_2$ are the slightly different selected angles, then the measured signal is:

$$dz = \frac{x'_2 - x'_1}{g_y} \cdot \frac{1}{\tan\alpha_1 + \tan\alpha_2}$$

This relationship ensures that the measurement of dz remains uncoupled with the measurement of x even in the case of a slight uncertainty in the mounting of the slots.

$$x = \frac{x'_1 - x'_2}{2g_y} + dz \cdot \frac{\tan\alpha_2 + \tan\alpha_1}{2}$$

If $\tan\alpha_1$ and $\tan\alpha_2$ are not perfectly known, the x coordinate might be slightly polluted by the z variations. Tuning $\alpha_1$ and $\alpha_2$ so that their amplitude is really equal reduces this defect.

Figure 4:
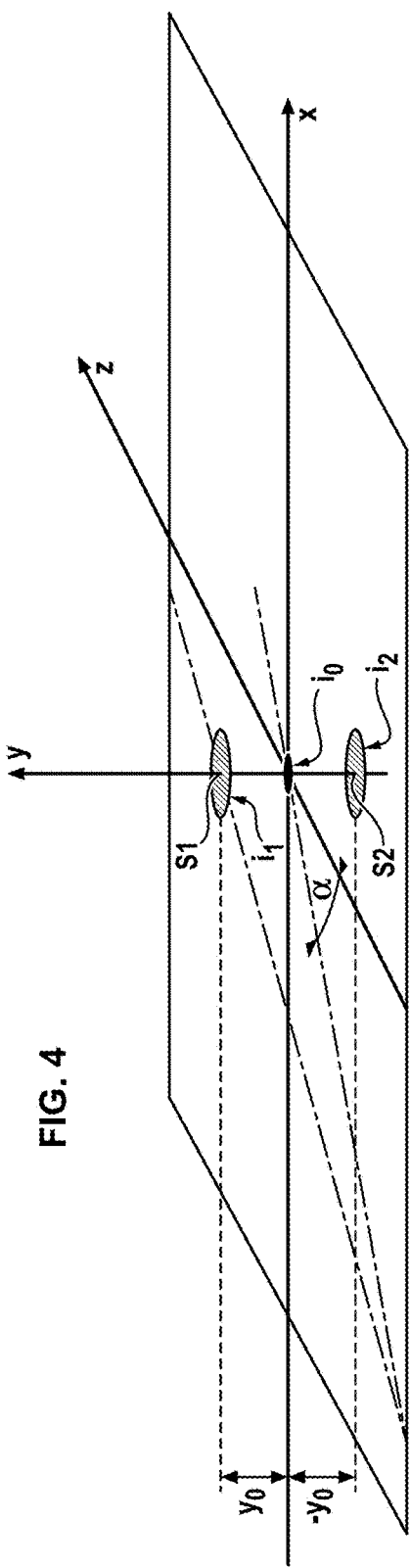

As illustrated on FIG. 4, when the bead B is located in the object plane of the imaging system, the image of the bead is located at the image plane of the imaging system, which is also the detector plane, so that $x_1=x_2=0$. However, the first image S1 of the bead is translated by the separating arrangement 9 along the third axis y by a constant value $+y_0$ while the second image S2 of the bead is translated by the separating arrangement 9 along the third axis y by a constant value $-y_0$. This allows to avoid overlapping of the spots S1 and S2 and precisely measuring the position z of the bead around the object plane of the imaging system.

Figure 5:
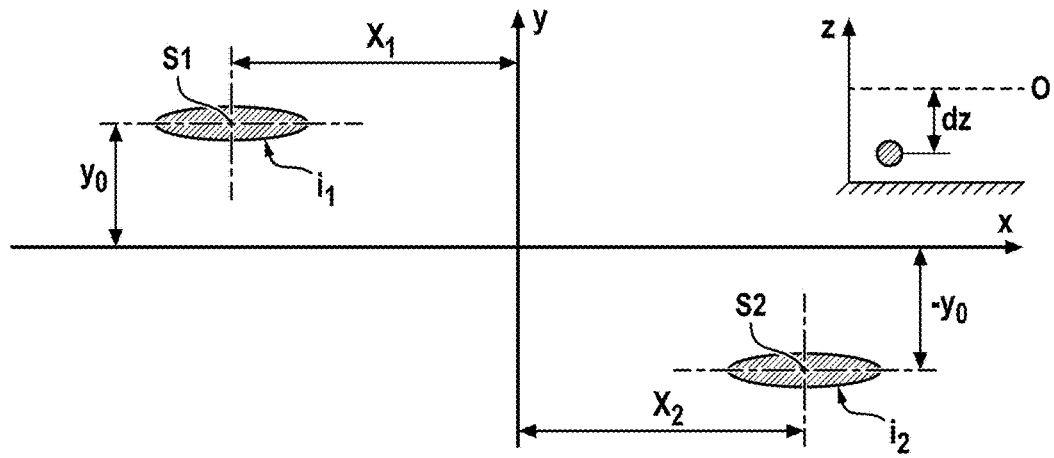
Figure 6:
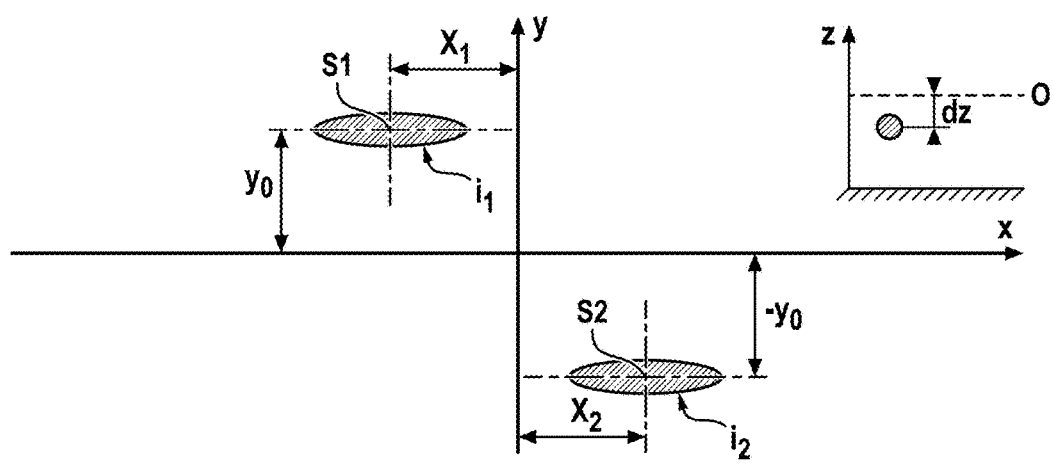

FIGS. 5 and 6 illustrate two images generated by the detector 6 for two different values of the position of the bead along the first axis z. Each image includes two spots S1 and S2. In both images, the spots are separated from each other by a constant distance equal to $2y_0$ along the third axis y.

The processing module 7 (illustrated on FIG. 1) is configured for processing the image generated by the detector 6 so as to determine a position of the bead B along axes x, y and z from the image generated by the detector 6.

Figure 23:
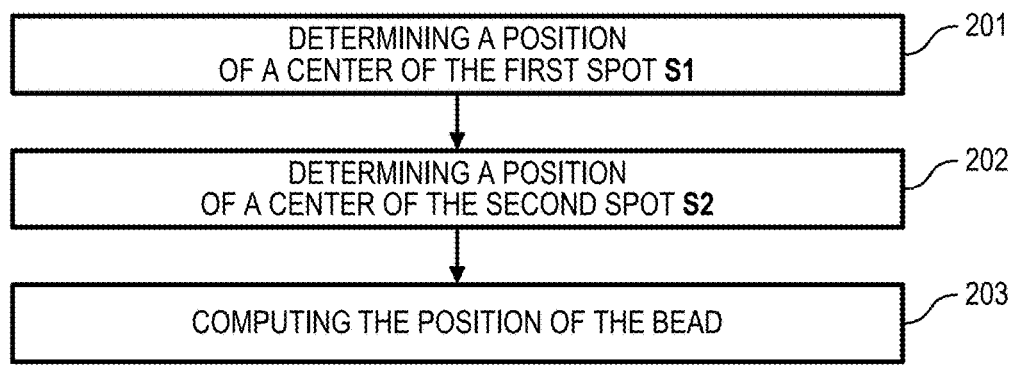
FIGS. 23 and 24 are diagrams illustrating different steps carried out by a processing module for processing an image generated by an optical device, according to the first embodiment of the invention.

To this end, the processing module 7 carries out the steps illustrated on FIG. 23:

according to a first step 201, the processing module 7 determines a position of a center of the first spot S1 in the image (i.e. coordinates $x'_1$ and $y'_1$), according to a second step 202, the processing module 7 determines a position of a center of the second spot S2 in the image (i.e. coordinates $x'_2$ and $y'_2$), and according to a third step 203, the processing module 7 computes the position of the bead B as a function of the positions of the center of the first spot and of the position of the center of the second spot.

The position of the bead along the third axis y is computed as:

$$y = \frac{y'_1 + y'_2}{2g_y}$$

where $(x'_1, y'_1)$ are coordinates of the center of the first spot S1, $(x'_2, y'_2)$ are coordinates of the center of the second spot S2 in the plane of the detector and a is the angle of the selected radiations relative to the optical axis O.

Figure 24:
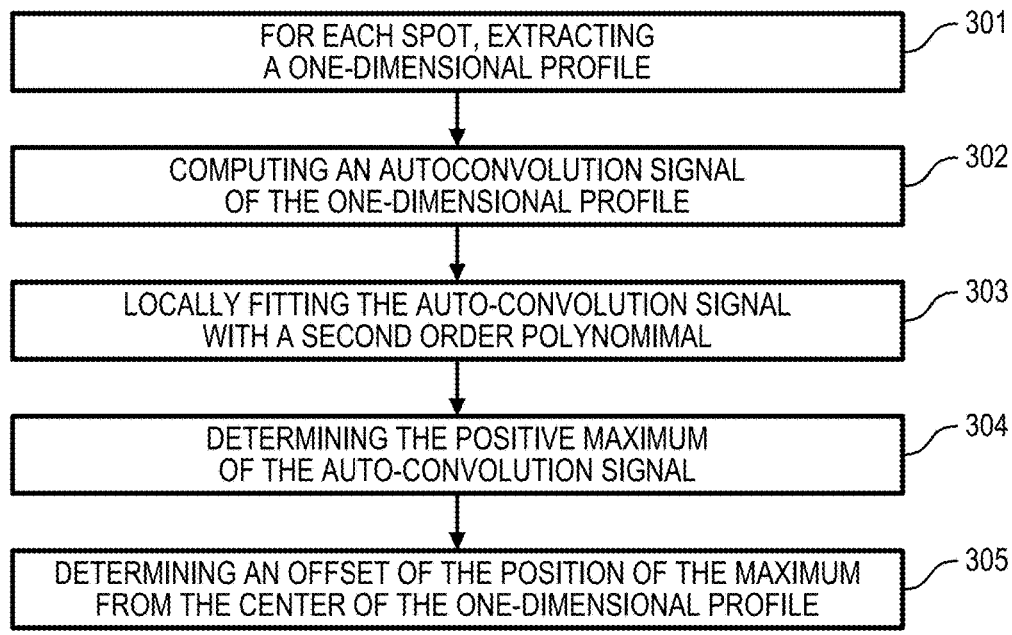
Figure 25:
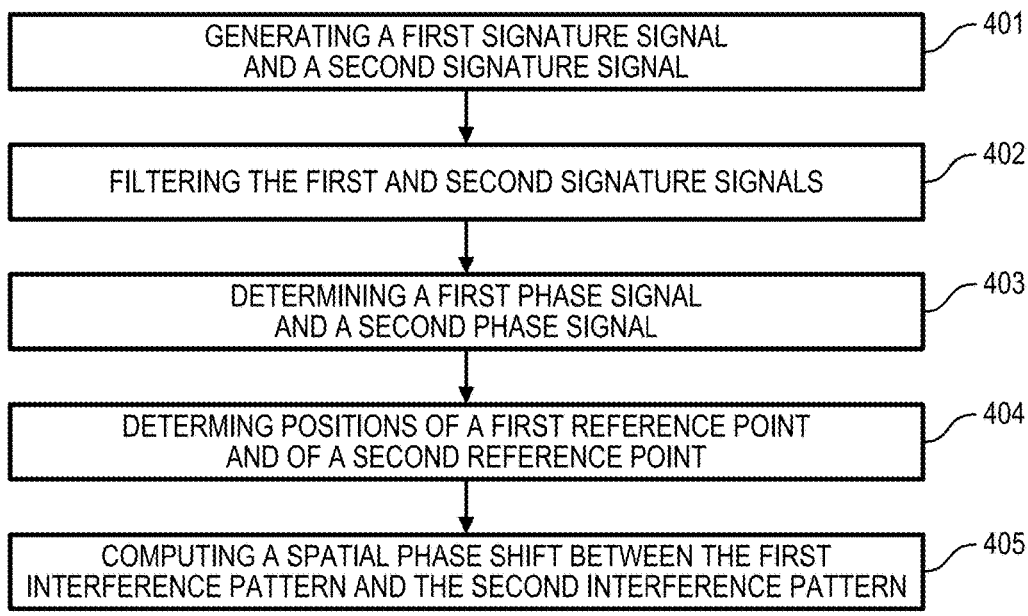
FIGS. 25 to 27 are diagrams illustrating different steps carried out by a processing module for processing an image generated by an optical device, according to the second embodiment of the invention.

As illustrated on FIG. 24, the position of the center of each spot is determined by computing the autoconvolution of one-dimensional profiles extracted from the image. For each spot and for the two axis x and y, a one-dimensional profile is extracted from the image (step 301) by averaging the pixels of the image along the perpendicular axis (for example, to compute the position $x'_1$, the lines of pixels of a part of the image which contains the spot S1 are averaged which provides a one-dimensional signal along x for the spot S1). Then for each extracted one-dimensional profile, an autoconvolution signal is computed (step 302) by computing the inverse Fourier Transform of the square of the Fourier Transform of the one dimensional profile.

The auto-convolution signal resulting from such an auto-convolution presents a positive maximum which position offset versus the center of the extracted profile is twice the offset of the spot from the center of the profile. Thus by determining this offset by locally fitting the auto-convolution signal with a second order polynomial for the four one-dimensional profiles (step 303), the processing module 7 determines the four coordinates $x'_1$, $y'_1$, $x'_2$ and $y'_2$ (steps 304 and 305).

The precision of the measurement depends on the characteristic size of the spots and on the number of photons used to generate the spots. The number of photons depends on the number of pixels covered by the spot and on the maximum possible number of detectable photons per pixel before saturation (i.e. "the well depth").

Precision of the determination of the center of a spot is proportional to:

$$\frac{\sigma}{\sqrt{N}}$$

where σ is the width at half maximum of the spot size, the shape of the spot being considered as Gaussian in a first approximation, and N is the total number of photons contained in the spot. σ is determined by the dimensions of the slots letting the radiations pass through the transmission mask.

Figure 7:
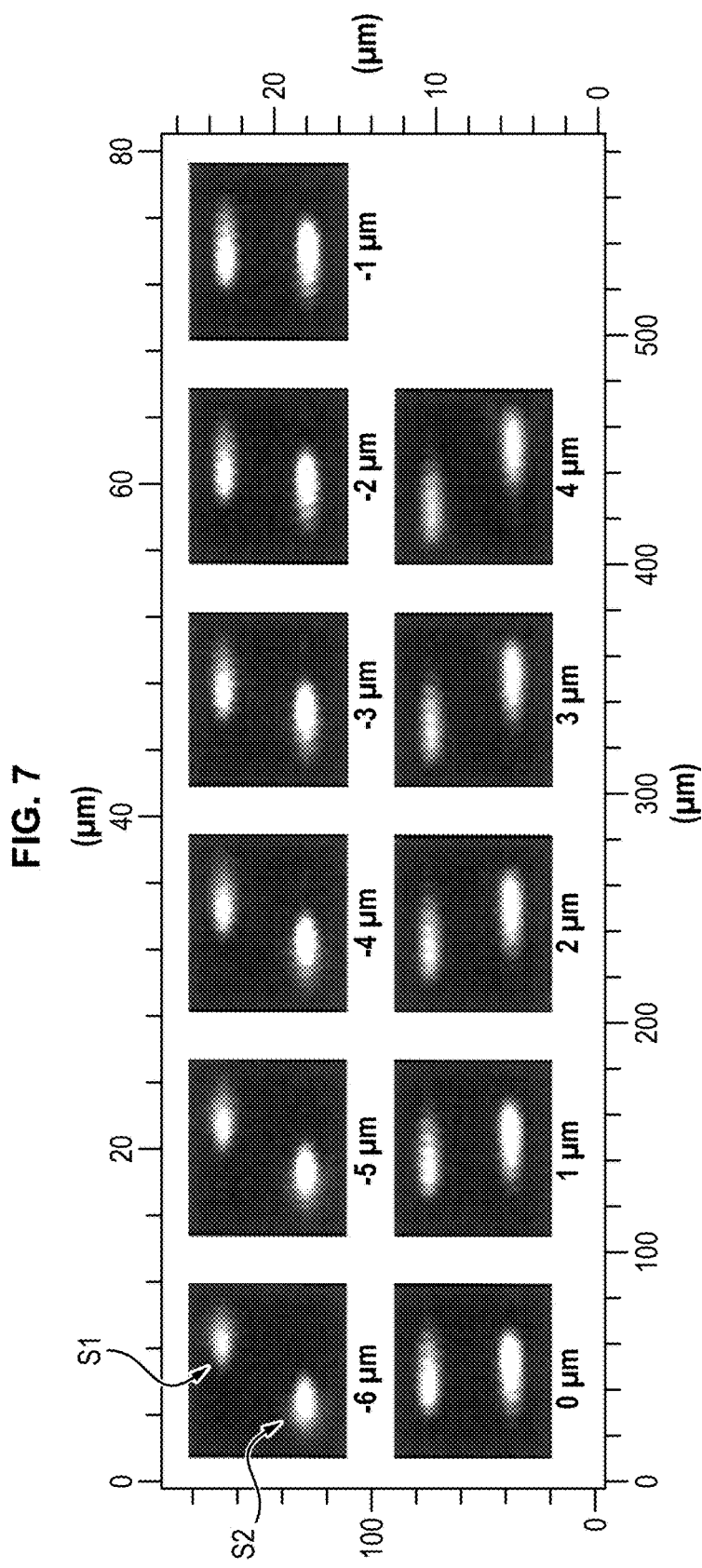
FIG. 7 shows different images generated by the detector for different positions of the bead, obtained with the device of FIG. 2.

FIG. 7 shows different images which have been generated by the detector 6 for different positions of the beads along the axis z. The bead was a paramagnetic bead having a diameter of 1 micrometer. The images have been obtained with an optical imaging system having a magnification factor $g_y$ of 40, a transmission mask having two slots and a separating arrangement comprising two inclined glass blades arranged symmetrically around the axis x.

Figure 8:
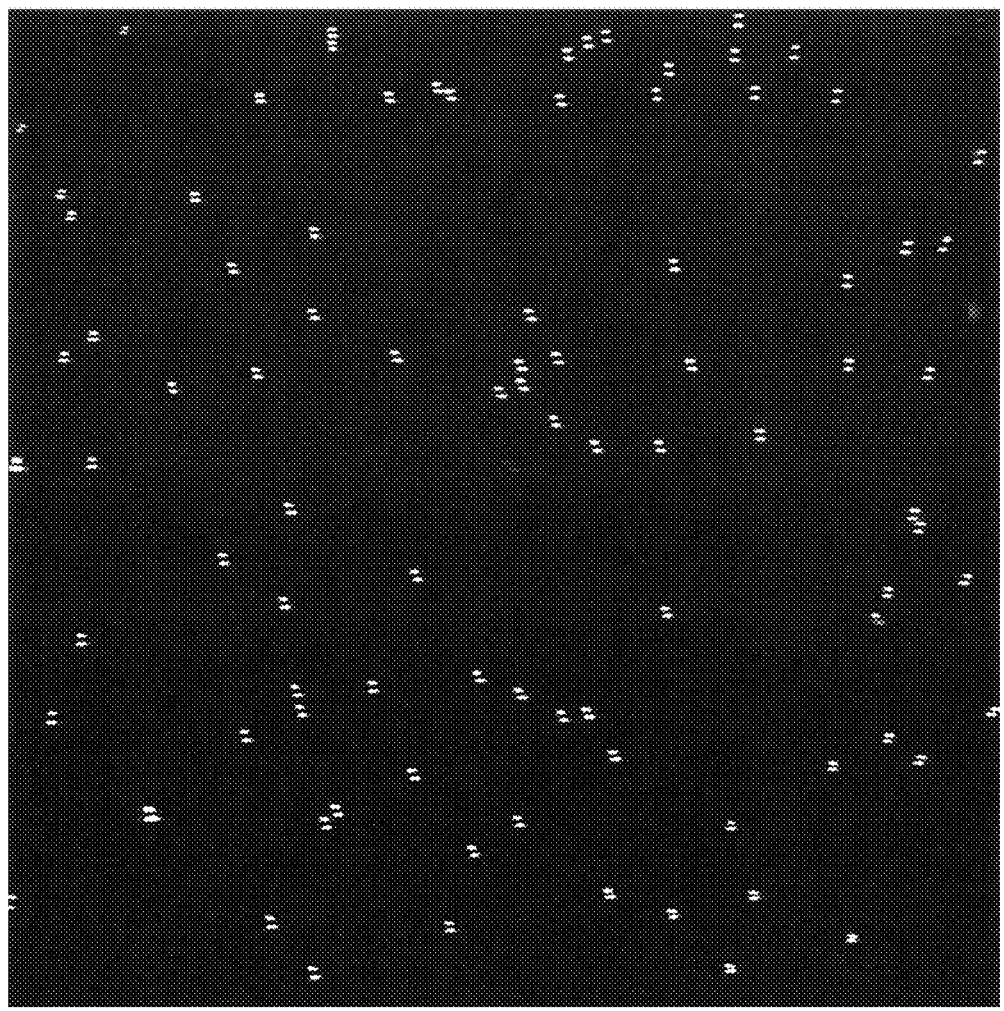
FIG. 8 shows an image generated by the detector for a batch of beads, obtained with the device of FIG. 2, FIGS. 9A and 9B diagrammatically show a device according to a second embodiment of the invention, comprising an amplitude mask, a separating arrangement comprising two blades and, wherein the imaging system comprises an infinity-corrected objective and a lens tube, FIGS. 10A, 10B and 10C diagrammatically show a device according to a third embodiment of the invention comprising an amplitude mask, a separating arrangement comprising two blades, and wherein the imaging system comprises a finite objective, FIGS. 11A and 11B diagrammatically show a device according to a fourth embodiment of the invention comprising an amplitude mask, a separating arrangement comprising two prisms, and wherein the imaging system comprises an infinity-corrected objective and a tube lens, FIG. 12 diagrammatically shows how the transmission mask blocks radiations coming directly from the light source, FIG. 13 diagrammatically shows a device according to a fifth embodiment of the invention, comprising an amplitude mask and a separating arrangement comprising two blades, and wherein the imaging system comprises an infinity-corrected objective, a 4F arrangement and a lens tube, FIG. 14 diagrammatically shows a device according to a sixth embodiment of the invention, comprising an amplitude mask, a separating arrangement comprising two prisms, and wherein the imaging system comprises an infinity-corrected objective, a 4F arrangement and a tube lens.

FIG. 8 shows an image which has been generated by the detector for a batch of beads. Each bead was a paramagnetic bead having a diameter of 1 micrometer. The image has been obtained with an optical objective having a magnification factor $g_y$ of 20, a transmission mask having two slots and a separating arrangement comprising two inclined glass blades arranged symmetrically around the axis x. The beads were placed in a microfluidic chamber substantially at the same position according to the axis z. The field of view was 628×628 micrometers. The image shows several pairs of spots, each pair of spots corresponding to one bead.

Figure 9A:
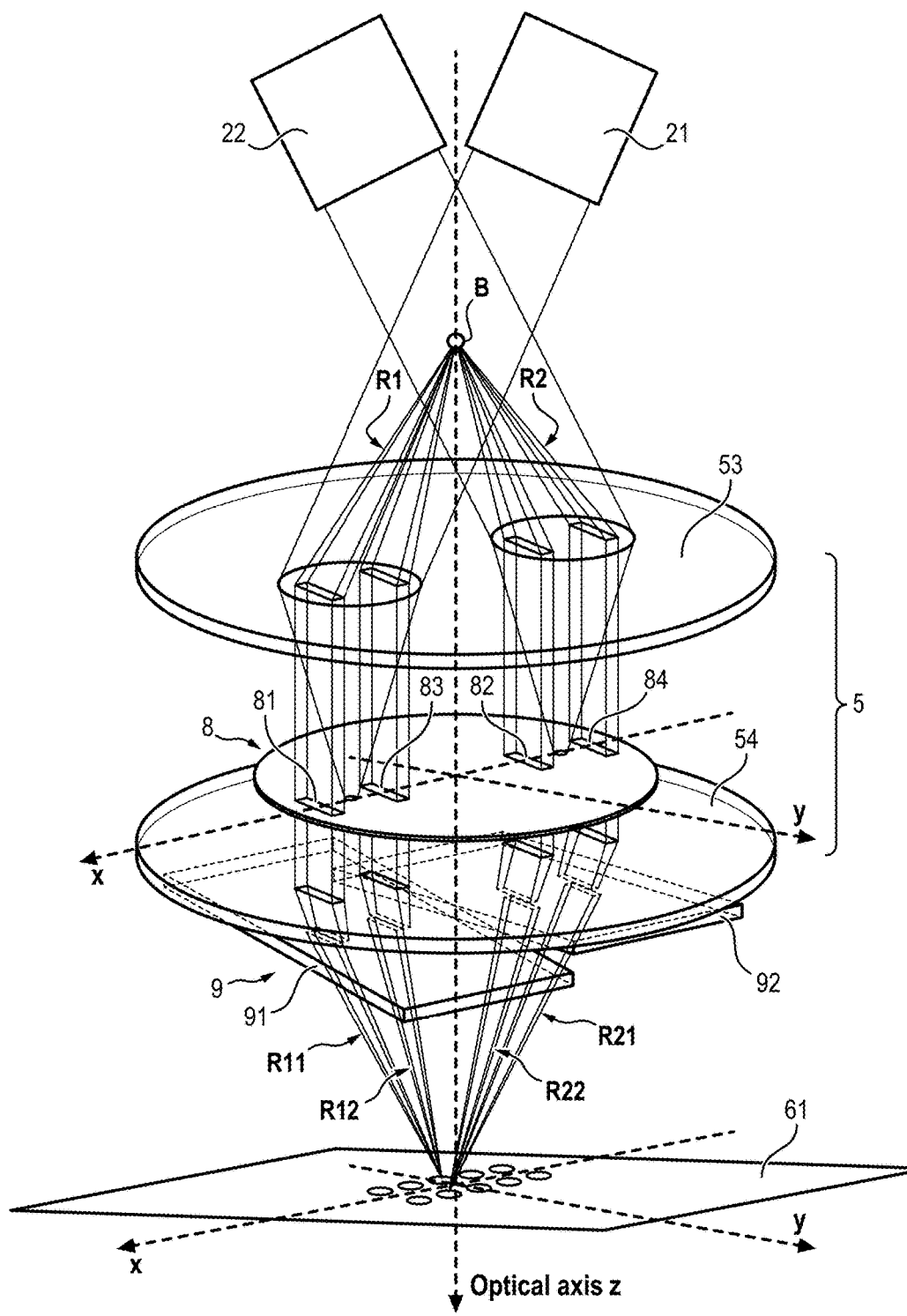
Figure 9B:
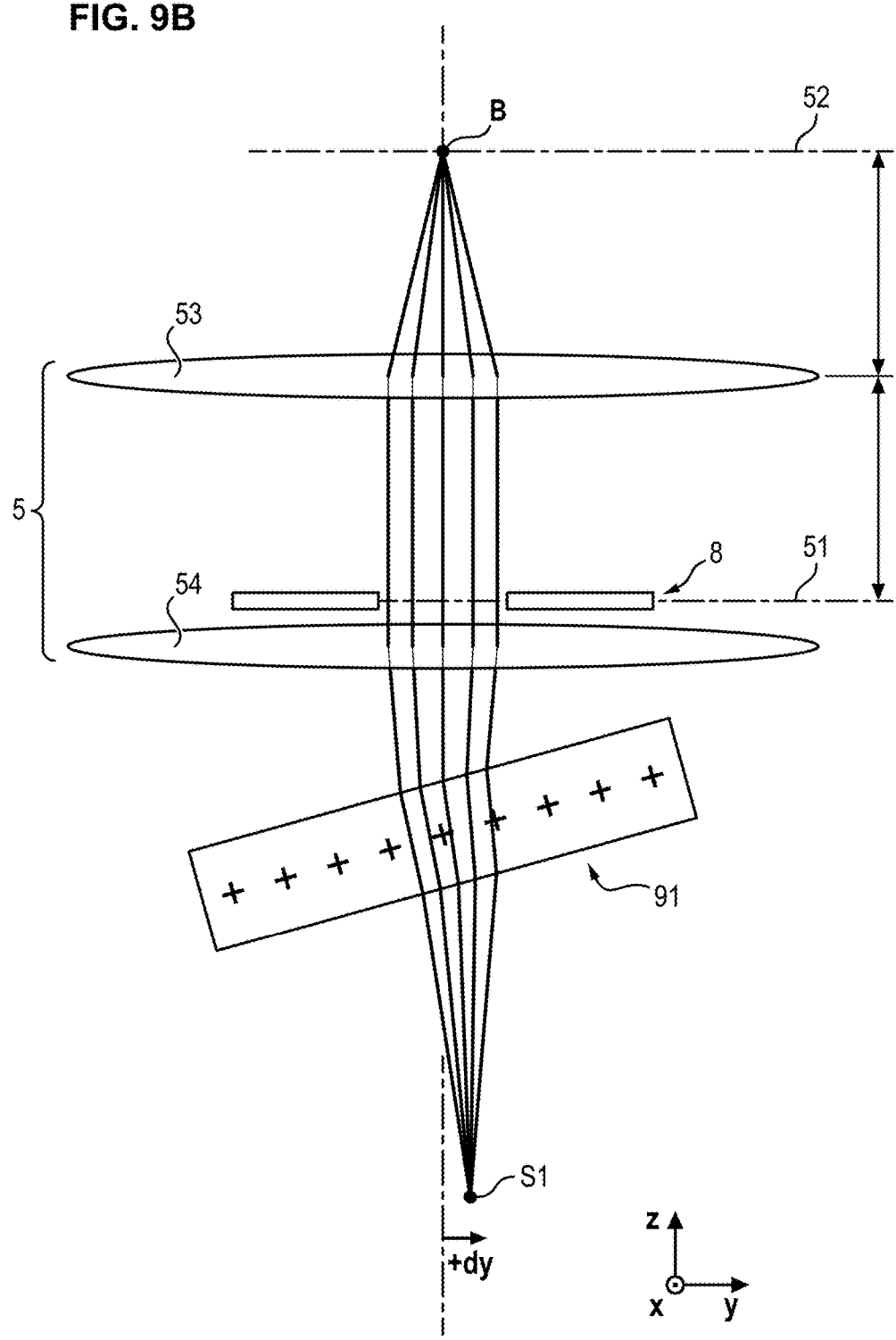

FIGS. 9A and 9B illustrate a second embodiment of an optical device 1 according to the invention.

In this second embodiment, the transmission mask 8 comprises two pairs of apertures 81, 83 and 82, 84.

The transmission mask 8 comprises a first pair of apertures 81, 83 dividing the first part R1 of the radiations into two first beams R11 and R12, and a second pair of apertures 82, 84 dividing the second part R2 of the radiations into two second beams R21 and R22. The first pair of apertures 81, 83 consists of a first pair of slots and the second pair of apertures 82, 84 consists of a second pair of slots.

In addition, the device comprises two light sources 21 and 22 arranged for illuminating the bead B according to two different angles. The light sources 21 and 22 are arranged so as to direct light radiations toward the bead B according to a first angle and according to a second angle respectively.

More precisely, the first light source 21 generates first light radiations which are directed between the apertures 81, 83 of the first pair of apertures. In the same way, the second light source 22 generates second light radiations which are directed between the apertures 82, 84 of the second pair of apertures.

With this arrangement, a part of the first light radiations which is diffused by the bead B is allowed to pass through the apertures 81, 83 of the first pair of apertures, while the part of the first light radiations coming directly from the first light source 21 impacts the amplitude mask 8 between the apertures 81, 83 and is blocked.

Similarly, the second light source 22 is arranged so that a part of the second light radiations which is diffused by the bead B is allowed to pass through the apertures 82, 84 of the second pair of apertures, while the part of the second light radiations coming directly from the second light source 22 impacts the amplitude mask between the apertures 82, 84 and is blocked.

In the second embodiment shown on FIGS. 9A and 9B, the optical imaging system 5 comprises an infinity-corrected objective 53 (i.e. the optical objective has an image distance that is set to infinity) and a tube lens 54. In other words, the image of an object positioned at the object focal plane of the optical objective 53 (which is also the object plane of the optical imaging system 5) does not form an image but is converted by the optical objective 53 into an infinity parallel beam. The tube lens 54 is adapted for focusing parallel beams produced by the optical objective 53 on the image plane of the optical imaging system 5.

As illustrated on FIGS. 9A and 9B, the separating arrangement 9 comprises two blades 91, 92.

Each blade has parallel faces which are inclined relative to a plane x, y perpendicular to the first axis z. More precisely, the blades include a first blade 91 which is inclined of a first angle and a second blade 92 which is inclined of a second angle, opposite to the first angle. The first blade 91 and the second blade 92 are arranged so that the first part of the light radiations goes through the first blade 91 and the second part of the radiation goes through the second blade 92. In this manner, the first beams R11, R12 and the second beams R21, R22 coming from the apertures 81, 83 and 82, 84 respectively are translated along the third axis y in opposite directions.

The tube lens 54 is adapted for focusing each infinity parallel beam R11, R12, R21, R22 on an image plane.

The two first beams R11 and R12 impact the detector plane, thus forming a first spot S1. The two second beams R21 and R22 impact the detector plane, thus forming a second spot S2.

Moreover, the two first beams R11 and R12 interfere with each other so as to create a first interference pattern within the first spot S1. Similarly, the two second beams R21 and R22 interfere with each other so as to create a second interference pattern within the second spot S2.

Figure 10A:
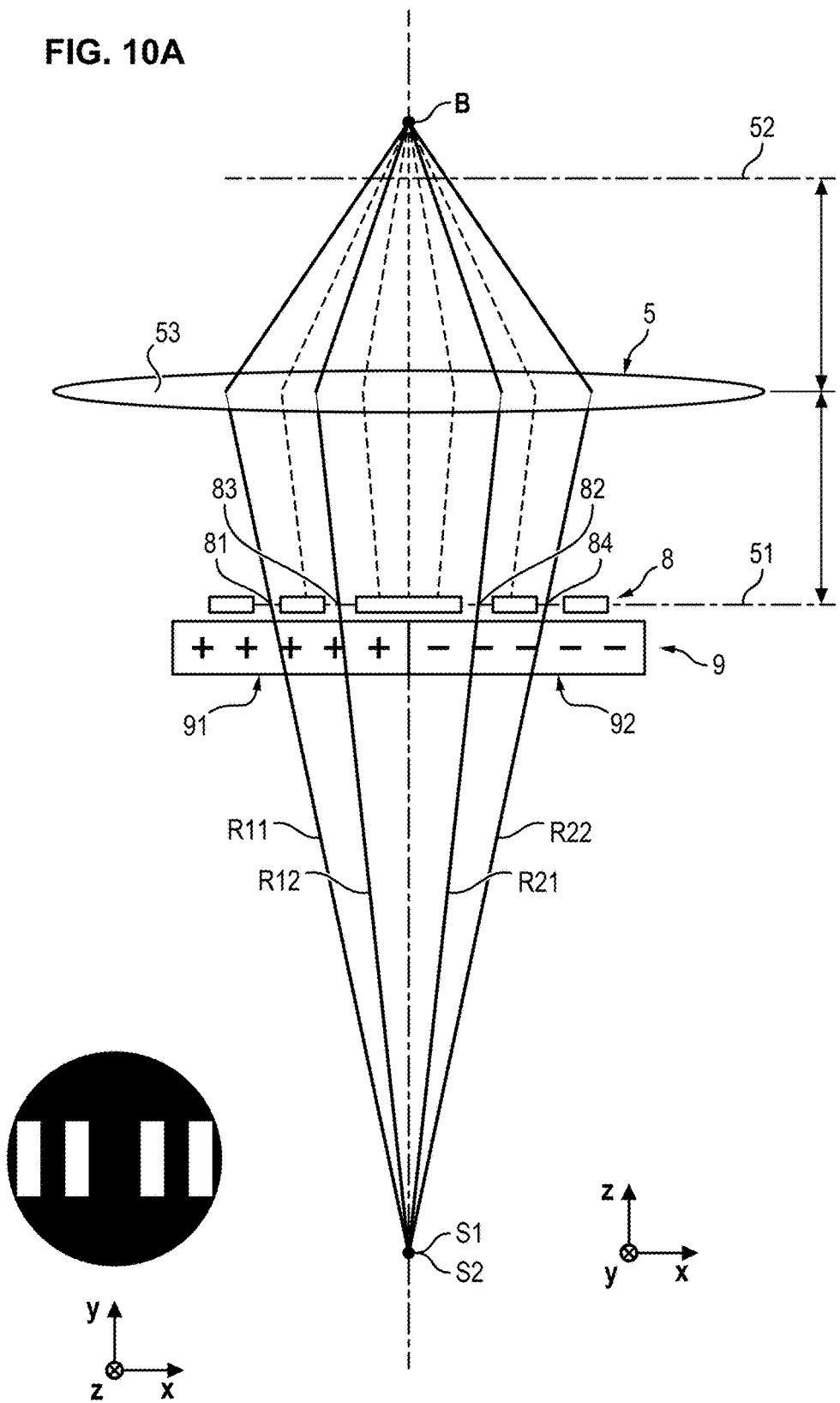
Figure 10B:
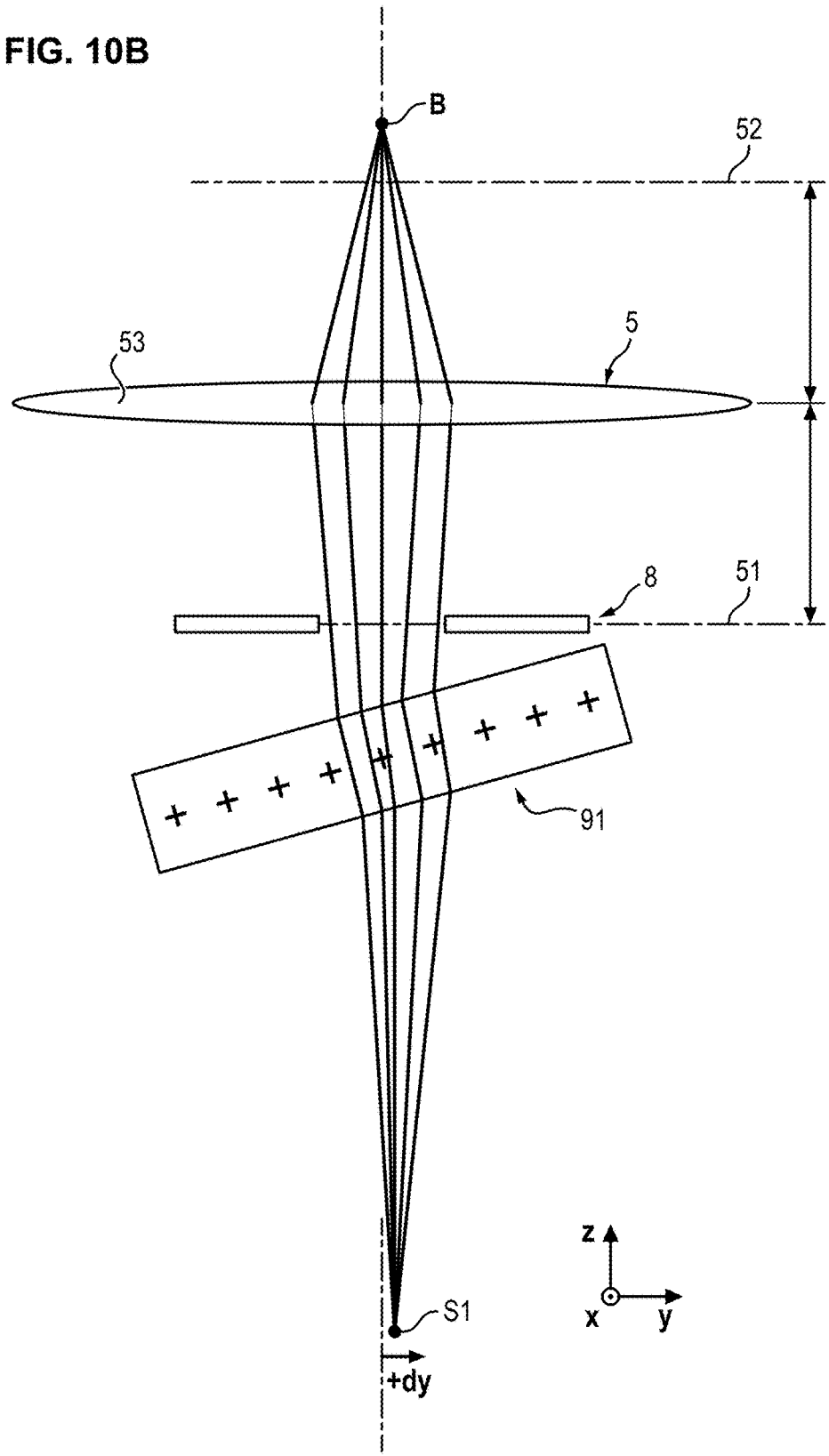
Figure 10C:
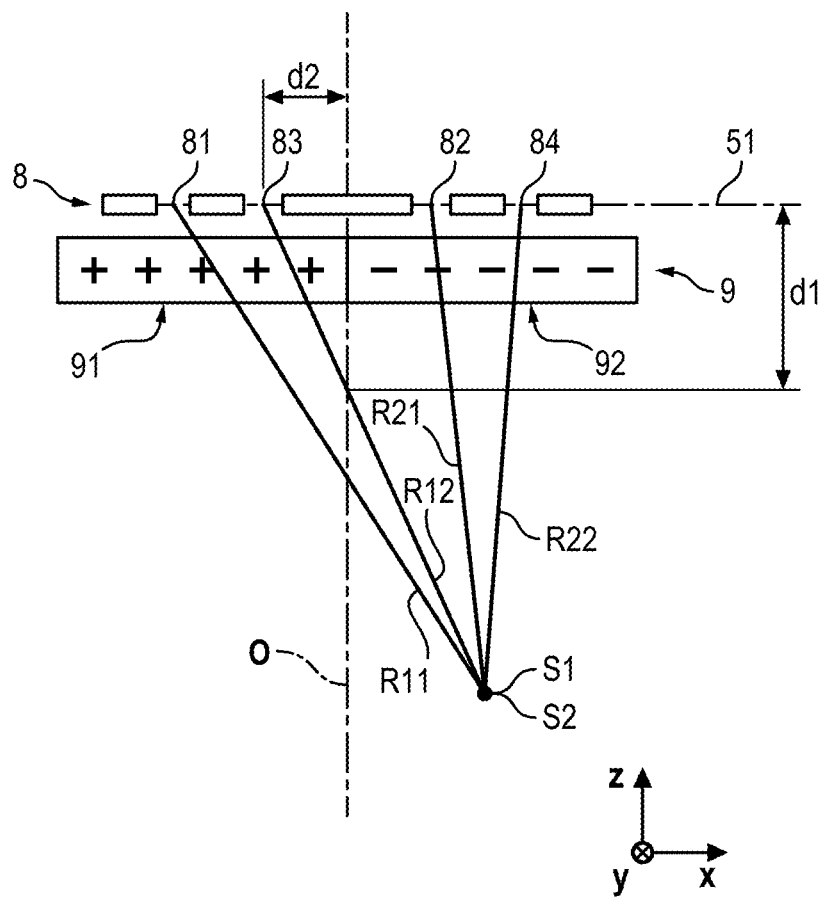

FIGS. 10A, 10B and 10C diagrammatically show a device according to a third embodiment of the invention.

According to this third embodiment, the optical imaging system 5 only comprises a finite objective 53 (i.e. an optical objective which has an image distance that is finite). In other words, the image of an object positioned at the object plane of the optical objective form an image positioned in an image plane.

As in the first embodiment, the separating arrangement 9 comprises two blades 91 and 92.

As in the first embodiment, each blade has parallel faces which are inclined relative to a plane x, y perpendicular to the first axis z. More precisely, the blades include a first blade 91 which is inclined of a first angle and a second blade 92 which is inclined of a second angle, opposite to the first angle. The first blade 91 and the second blade 92 are arranged so that the first part of the light radiations goes through the first blade 91 and the second part of the radiation goes through the second blade 92. In this manner, the first beams R11, R12 and the second beams R21, R22 coming from the apertures 81, 83 and 82, 84 respectively are translated along the third axis y in opposite directions.

As shown on FIGS. 10A and 10B, the optical imaging system 5 has a back focal plane 51 (or Fourier plane) and an object plane 52. The transmission mask is positioned in the back focal plane 51 of the imaging system 5 so as to select parts of the light radiations which have been diffused by the object according to predetermined angles. Depending on the numerical aperture of the optical objective, the predetermined angles may be equal or greater than 45° or 50°.

As shown on FIG. 10C, the maximum distance d1 between the blades 91, 92 and the back focal plane 51 along the optical axis O is such that all first beams R11 and R12 go through the first blade 91 and all second beams R21 and R22 go through the second blade 92.

The maximum distance d1 depends on the distance d2 between the aperture 83 (or 82) which is the closest to the optical axis O and the optical axis O.

The plane where the separating arrangement is located is determined by the maximum angle θ of the radiations emitted by the bead when the bead is located in the border of the field-of-view of the optical objective at this plane, and by the position p along the second axis x of the part of the transmission mask which is closest to the first axis, the maximum distance being $$d1 = \frac{p}{\tan\theta}.$$

Figure 11A:
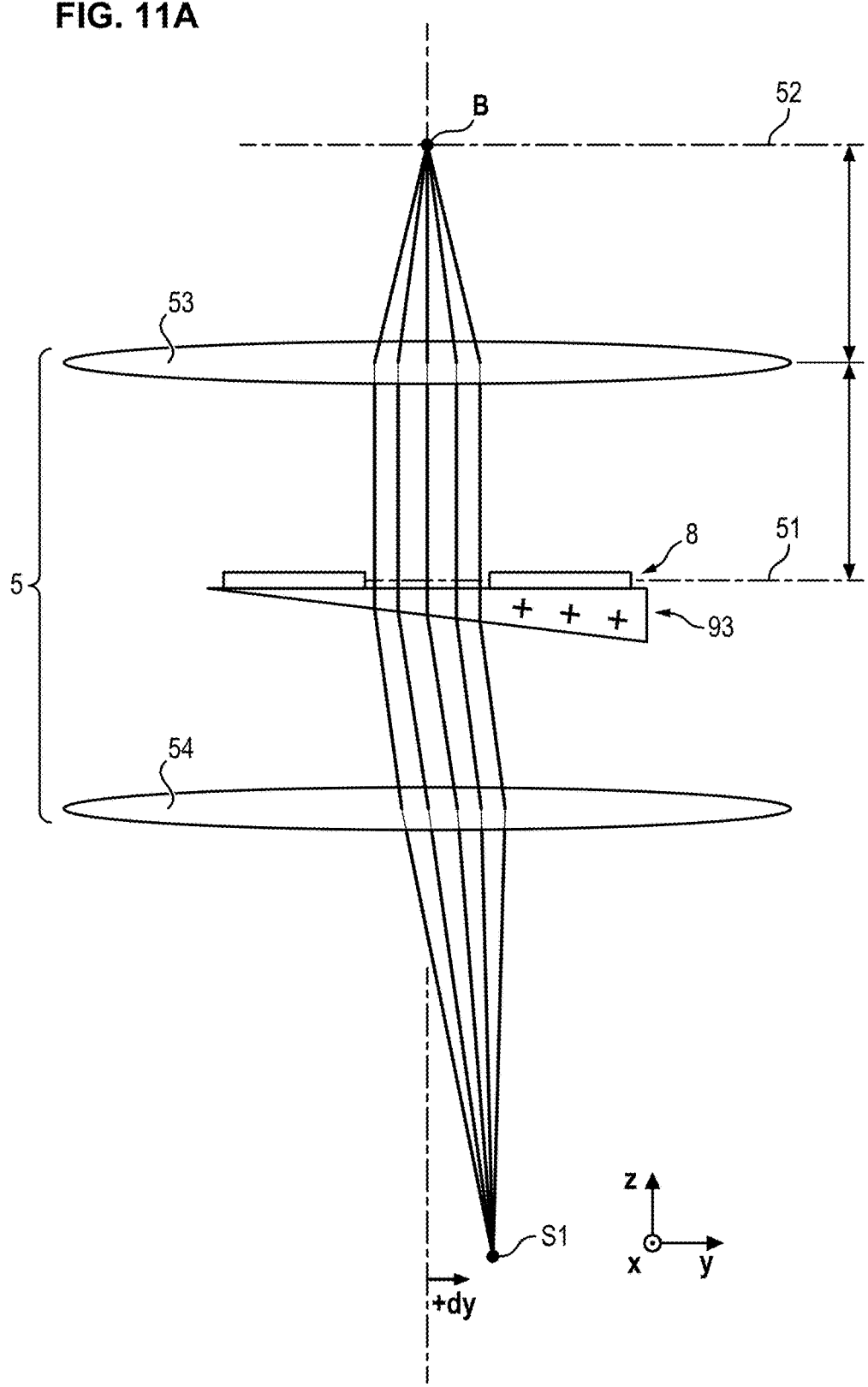
Figure 11B:
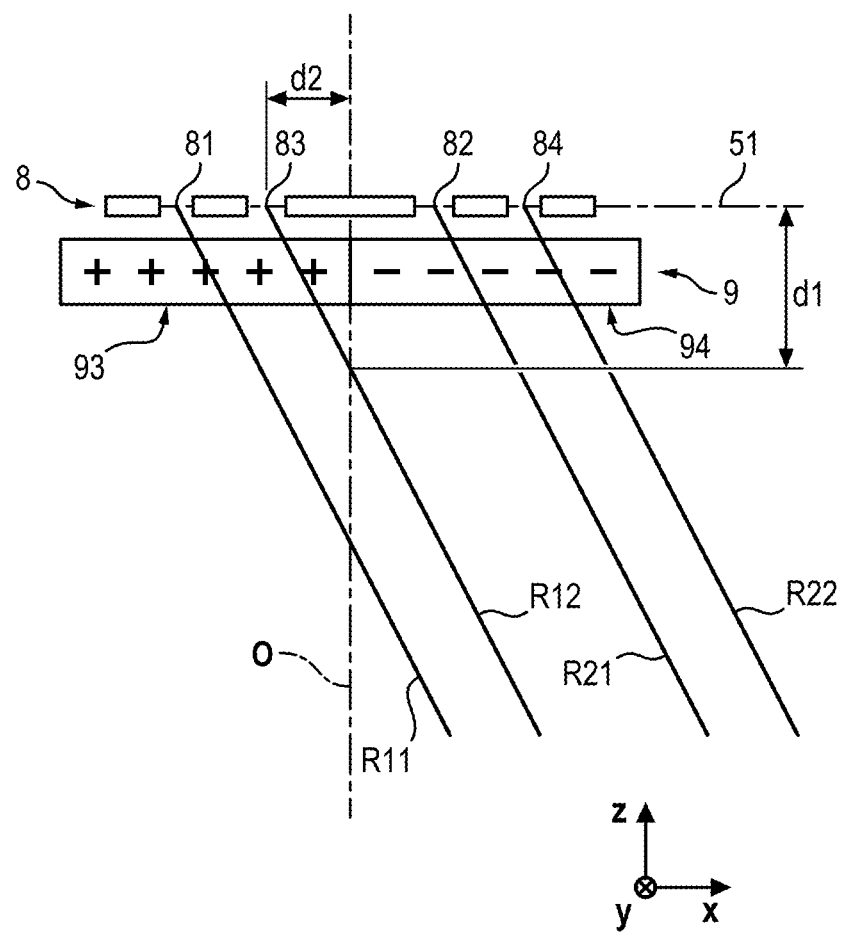

FIGS. 11A and 11B diagrammatically show a device according to a fourth embodiment of the invention wherein the imaging system 5 comprises an infinity-corrected objective 53 and a tube lens 54.

In this embodiment, the separating arrangement 9 comprises two prisms 93, 94.

The first prism 93 and the second prism 94 are positioned between the transmission mask 8 and the tube lens 53. The prisms 93 and 94 are arranged so that the first part R1 of the light radiations goes through the first prism 93 and is deviated by the first prim 93. The second part R2 of the radiation goes through the second prism 94 and is deviated by the second prism 94. Deviation of the two parts R1 and R2 of the radiations are converted into translations by the tube lens 53. In this manner, the first beams R11, R12 and the second beams R21, R22 are translated along the third axis y in opposite directions.

As shown on FIG. 11B, the maximum distance d1 between the prisms 93, 94 and the back focal plane 51 along the optical axis O is such that all first beams R11 and R12 go through the first prism 95 and all second beams R21 and R22 go through the second prism 94.

The maximum distance d1 depends on the distance d2 between the aperture 83 (or 82) which is the closest to the optical axis O and the optical axis O.

Figure 12:
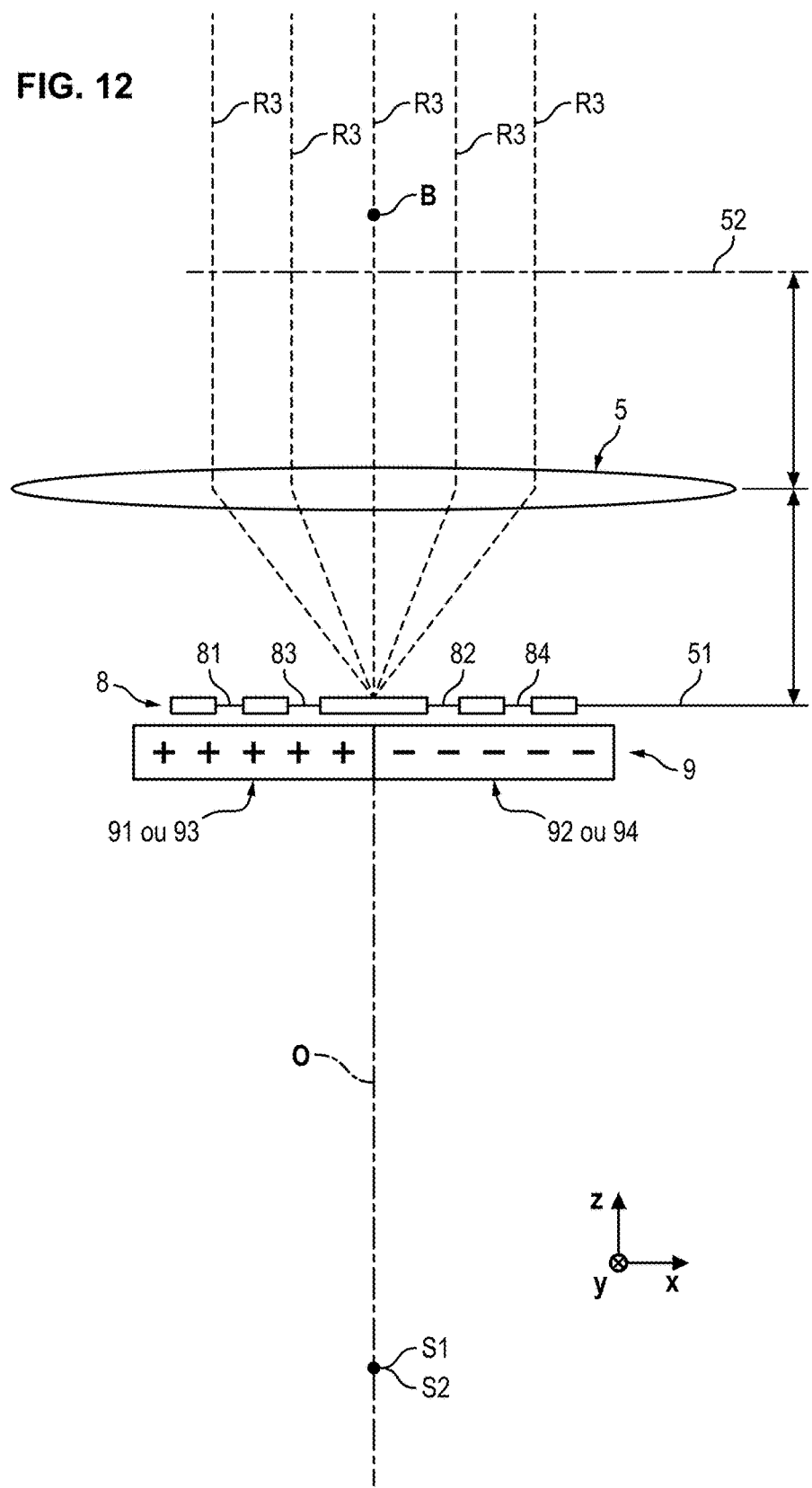

FIG. 12 diagrammatically shows how the transmission mask 5 blocks light radiations R3 coming directly from the light source, assuming the light source is positioned on the optical axis O, Light radiations R3 which are emitted by the source and which are not diffused by the bead B, propagate parallel to the optical axis. These radiations R3 are focused by the optical imaging system 5 in the back focal plane 51, between the apertures 83 and 82, in an area of the transmission mask which is opaque to the radiations.

Figure 13:
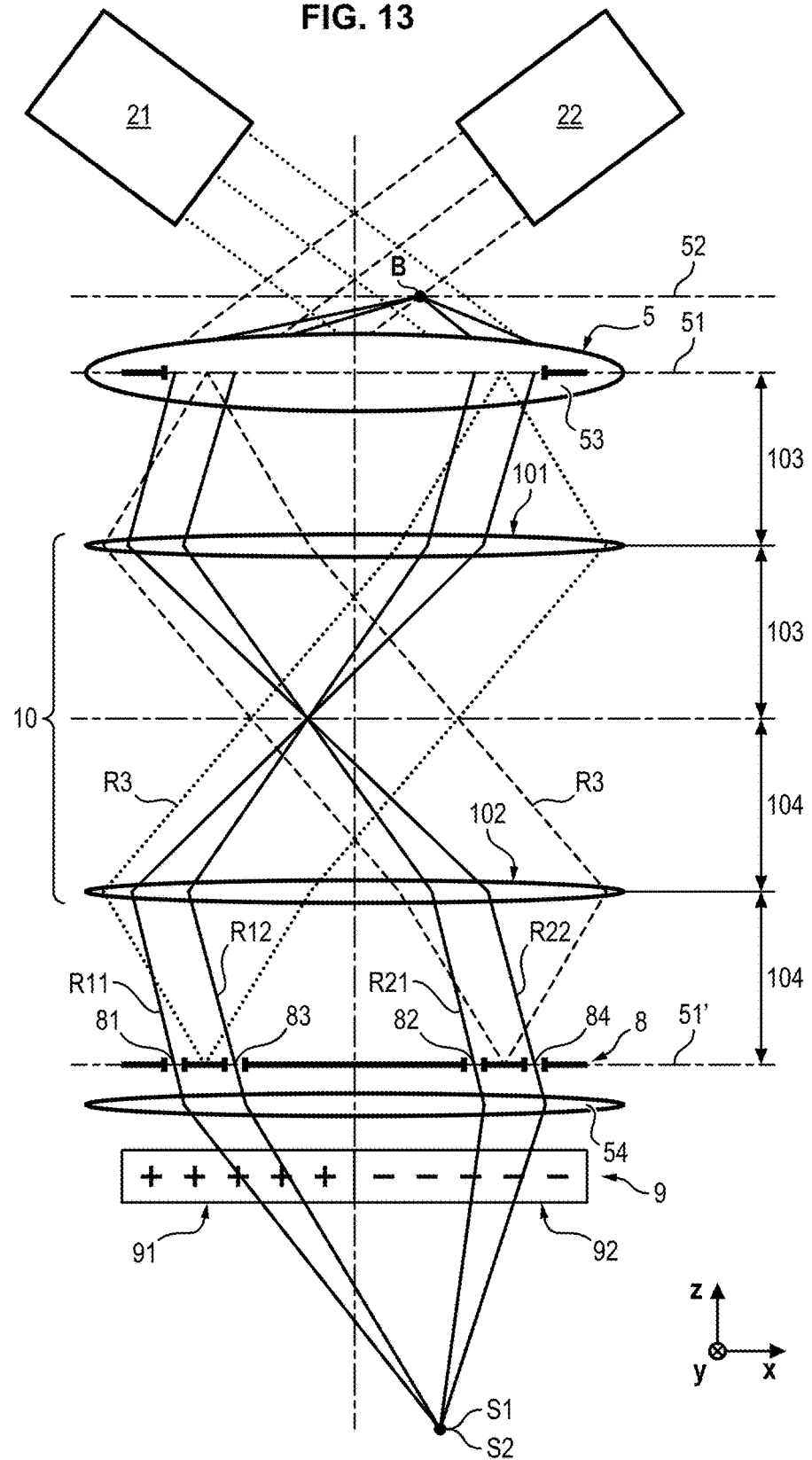

FIG. 13 diagrammatically shows a device according to a fifth embodiment of the invention.

According to this fifth embodiment, the device 1 comprises an imaging system 5. The optical imaging system 5 comprises an infinity-corrected objective 53, an optical relay 10 and a tube lens 54.

In this fifth embodiment, the back focal plane 51 is located inside the optical objective 53 and is not accessible for positioning the amplitude mask 8.

The optical relay 10 can be a 4F arrangement. The 4F arrangement 10 is positioned between the optical objective 53 and the transmission mask 8. The 4F arrangement 10 is configured to produce an image plane 51' of the back focal plane 51, outside the optical objective 53. The amplitude mask 8 is positioned in the image plane 51'.

The 4F arrangement 10 comprises a first lens 101 having a first focal length 103 and a second lens 102 having a second focal length 104. The first lens 101 and the second lens 102 may have different focal length. The first focal lens 102 is positioned relative to the optical objective 53, so that the object focal plane of the first lens 101 is located in the back focal plane 51 of the optical objective 53. The second lens 102 is positioned relative to the first lens 101 so that the object focal plane of the second lens 102 is located in the back focal plane of the first lens 101. As a result, the image plane 51' of the back focal plane 51 of the optical objective 53 is located in the back focal plane of the second lens 102.

As in the second embodiment of FIGS. 9A and 9B, the device 1 also comprises a separating arrangement 9. The separating arrangement comprises two blades 91 and 92, and the tube lend 54 is positioned between the amplitude mask 8 and the separating arrangement 9.

Figure 14:
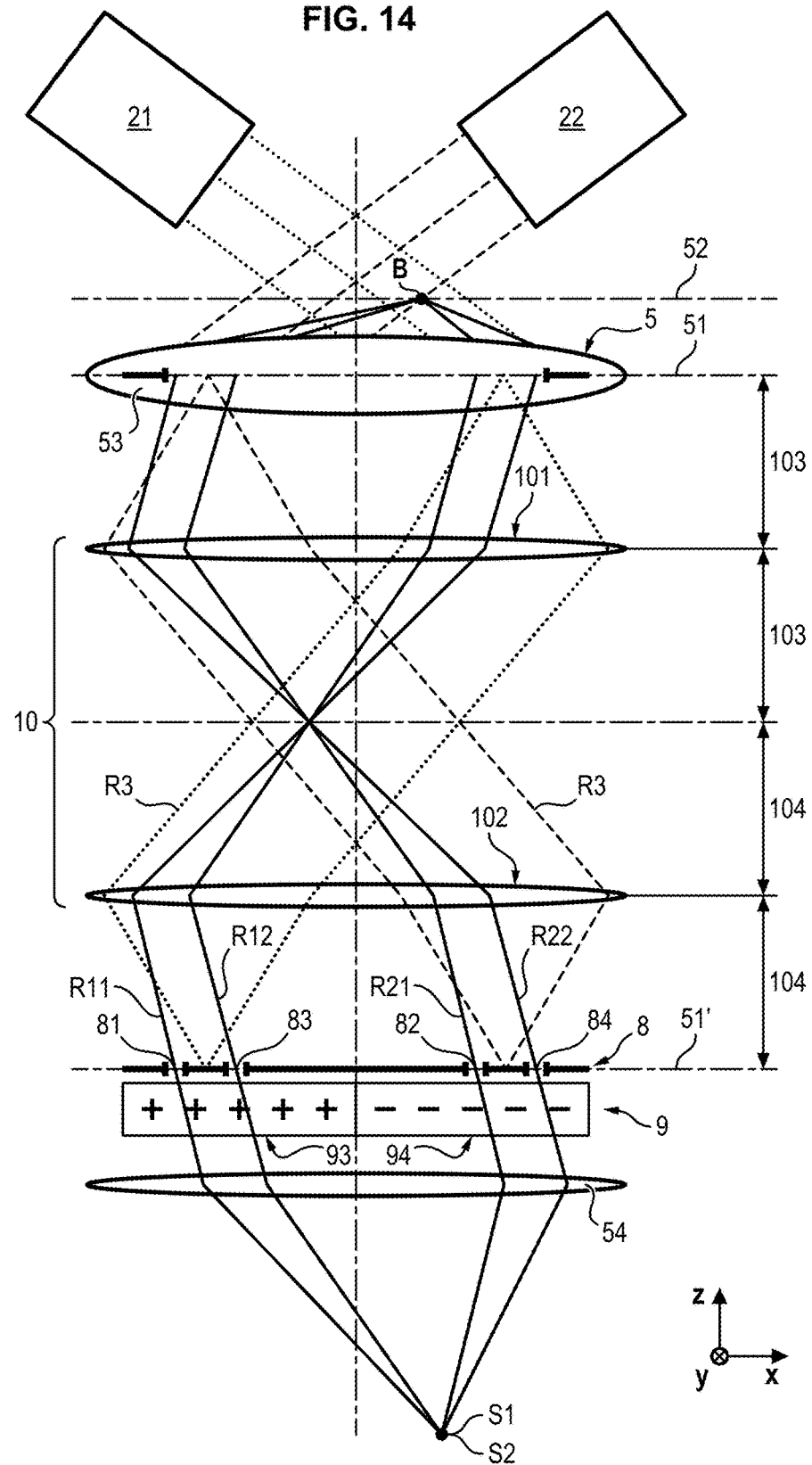

FIG. 14 diagrammatically shows a device 1 according to a sixth embodiment of the invention.

As in the fifth embodiment of FIG. 13, the device 1 comprises an imaging system 5 comprising an infinity-corrected objective 53, an optical relay 10 and a tube lens 54.

However, in this sixth embodiment, the device 1 comprises a separating arrangement comprising two prisms 93, 94, the prisms 93, 94 being positioned between the amplitude mask 8 and the tube lens 54.

Figure 15:
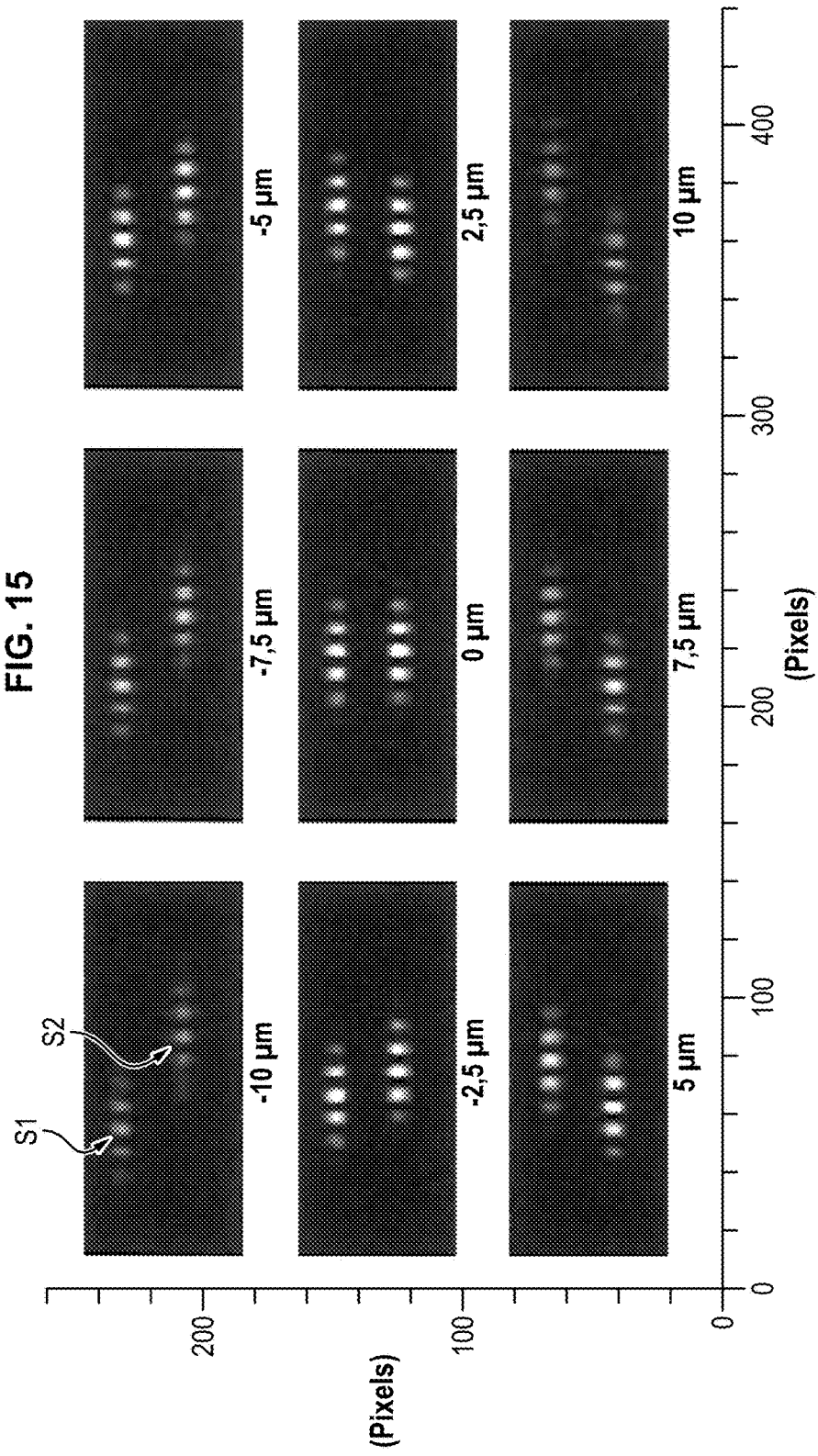
FIG. 15 shows different images generated by the detector for different positions of the bead, obtained with the device of FIG. 13.

FIG. 15 shows different images generated by the detector 6 for different positions of the bead B along the axis z, with the device of FIG. 13.

It is to be noted that similar images would be obtained with the devices of FIGS. 9 to 12 and 14.

As shown in FIG. 15, the two first beams R11 and R12 interfere with each other in the detector plane so as to create a first interference pattern within the first spot S1. The two second beams R21 and R22 interfere with each other in the detector plane so as to create a second interference pattern within the second spot S2. Each interference pattern comprises interferences fringes extending parallel to the axis y. Successive fringes of each interference pattern are spaced by a constant pitch i.

The processing module 7 (illustrated on FIG. 1) is configured for processing the image generated by the detector 6 so as to determine a position of the bead B in three dimensions, along axes x, y and z.

To this end, the processing module 7 determines a spatial phase shift between the first interference pattern and the second interference pattern along the second axis (x).

More precisely, the processing module carries out the steps illustrated on FIG. 23:

According to a first step 401, the processing module generates a first signature signal representative of a spatial variation of the intensity of the first spot (S1) along the second axis (x).

In the same way, the processing module generates a second signature signal representative of a spatial variation of the intensity of the second spot (S2) along the second axis (x).

Examples of a first signature signal and of a second signature signals are shown on FIGS. 19A and 19B (signals illustrated at the top of the figures).

According to a second step 402, the processing module filters the first signature signal and the second signature signal by applying a band-pass filter centered on the spatial frequency of the interference pattern. The spatial frequency is defined by the geometrical parameters of the optical device (in particular, the distance between the slots of a pair of slots of the transmission mask).

Examples of a filtered first signature signal and of a filtered second signature signal are shown on FIGS. 19A and 19B (signals illustrated at the middle of the figures).

According to a third step 403, the processing module applies a Hilbert transform to each filtered signal so as to generate a corresponding phase signal representative of the phase of the filtered signal. This step allows generating a first phase signal representative of the phase of the filtered first signal and of the phase of the filtered second phase signal.

Examples of a first phase signal and of a second phase signal are shown on FIGS. 19A and 19B (signals illustrated at the bottom of the figures).

According to a fourth step 404, the processing module determines for the first phase signal, a position $x_1$ of the corresponding first spot along the x axis. The position of the first spot is along the axis x is the position of a first reference point where the first phase signal is zero near the maximum amplitude of the filtered first signature signal.

In the same way, the processing module determines for the second phase signal, a position $x_2$ of the corresponding second spot along the x axis. The position of the second spot is along the axis x is the position of a second reference point where the second phase signal is zero near the maximum amplitude of the filtered second signature signal.

The first reference point and the second reference point are identified by arrows on FIGS. 19A and 19B.

According to a fifth step 405, the processing module compute the spatial phase shift between the first interference pattern and the second interference pattern as the distance $x_2-x_1$ along the second axis (x) between the first reference point and the second reference point.

The position of the bead along the first axis z is computed as a linear combination of $x_1$ and $x_2$. In particular, the position of the bead along the first axis z may be computed as proportional to the spatial phase shift $x_2-x_1$.

The position of the bead along the second axis x is computed as a linear combination of $x_1$ and $x_2$. In particular, the position of the bead along the second axis x may be computed as the mean of $x_1$ and $x_2$, i.e. $x=\frac{1}{2}(x_1+x_2)$.

Figure 26:
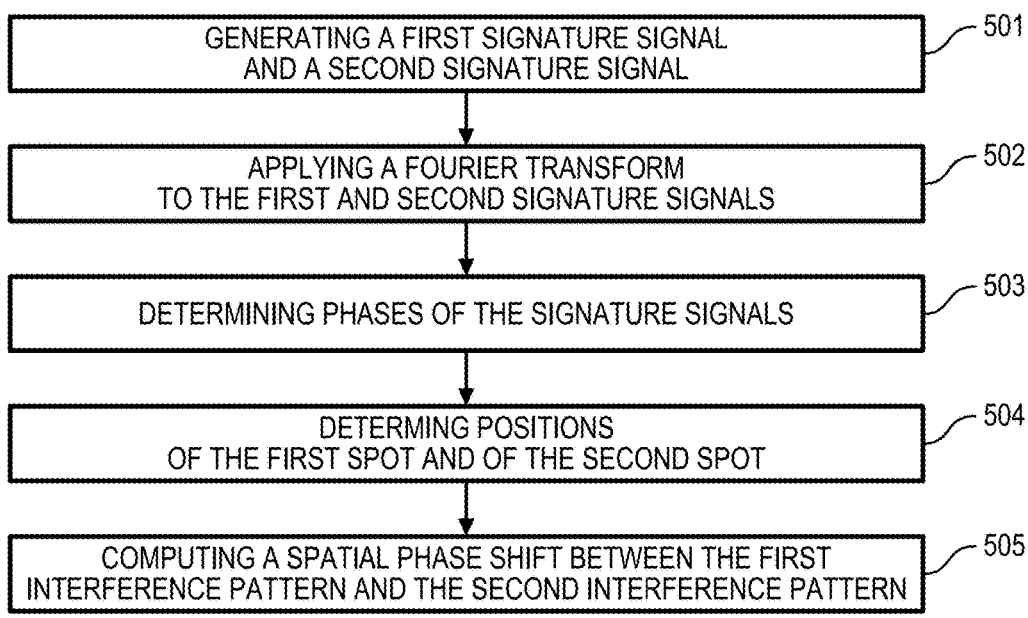

Alternatively, in order to determine the position of the bead along the first axis z and along the second axis x, the processing module 7 may carry out the steps illustrated on FIG. 26:

According to a first step 501, the processing module 7 generates a first signature signal representative of a spatial variation of the intensity of the first spot (S1) along the second axis (x).

In the same way, the processing module generates a second signature signal representative of a spatial variation of the intensity of the second spot (S2) along the second axis (x).

According to a second step 502, the processing module 7 computes a first Fourier transform signal by applying a Fourier transform to the first signature signal.

In the same way, the processing module computes a second Fourier transform signal by applying a Fourier transform to the second signature signal.

According to a third step 503, the processing module 7 determines a phase of the first signature signal from the first Fourier transform signal. To this end, the phase of the first signature signal is determined by identifying an amplitude peak of the first Fourier transform signal (corresponding to the spatial frequency of the interference pattern of the first spot) and linear fitting the phase of the first Fourier transform signal around the peak. The constant term of the resulting regression line (intercept of the regression line) is considered as the phase of the first signature signal.

The constant term of the resulting regression line is considered to be the phase of the first signature signal, but is undetermined by a multiple of $2\pi$ (for instance, the value of the phase signature signal may be $0,1+2n\pi$ while the correct value is $0,1$). The linear term of the resulting regression line (slope of the regression line) is used to determine a correction of the phase of the first signature signal.

In the same way, the processing module determines a phase of the second signature signal from the second Fourier transform signal. To this end, the phase of the second signature signal is determined by identifying an amplitude peak of the second Fourier transform signal (corresponding to the spatial frequency of the interference pattern of the second spot) and linear fitting the phase of the second Fourier transform signal around the peak. The constant term of the resulting regression line (intercept of the regression line) is considered as the phase of the second signature signal.

The constant term of the resulting regression line is considered to be the phase of the second signature signal, but is undetermined by a multiple of $2\pi$ (for instance, the value of the phase signature signal may be $0,1+2n\pi$ while the correct value is $0,1$). The linear term of the resulting regression line (slope of the regression line) is used to determine a correction of the phase of the second signature signal.

In other words, the processing module uses the linear term of the linear equation of the regression line to find the multiple of $2\pi$ to be added to correct the phase of the corresponding signature signal.

According to a fourth step 504, the processing module determines from the phase of the first signature signal, a position $x_1$ of the corresponding first spot along the x axis.

In the same way, the processing module determines from the phase of the second signature signal, a position $x_2$ of the corresponding second spot along the x axis.

According to a fifth step 505, the processing module computes the spatial phase shift between the first interference pattern and the second interference pattern as the distance $x_2-x_1$ along the second axis (x).

The position of the bead along the first axis z is computed as a linear combination of $x_1$ and $x_2$. In particular, the position of the bead along the first axis z may be computed as proportional to the spatial phase shift $x_2-x_1$.

The position of the bead along the second axis x is computed as a linear combination of $x_1$ and $x_2$. In particular, the position of the bead along the second axis x may be computed as the mean of $x_1$ and $x_2$, i.e. $x=\frac{1}{2}(x_1+x_2)$.

Figure 27:
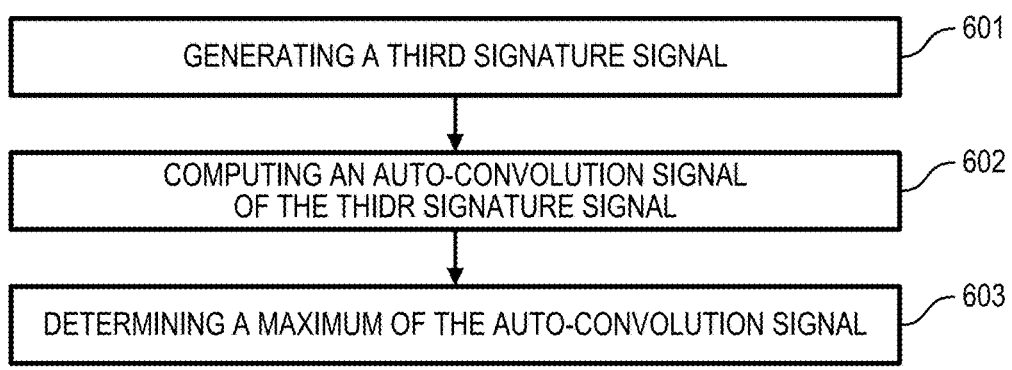

The position of the bead along the third axis y is determined as illustrated on FIG. 27.

According to a first step 601, the processing module 7 generates a third signature signal representative of a spatial variation of the intensity of the first spot (S1) and of the second spot (S2) along the third axis (y).

According to a second step 602, the processing module 7 computes the auto-convolution of the third signature signal. The auto-convolution of the third signature signal is computed by inverse Fourier transforming the square of the Fourier transform signal of the third signature signal.

According to a third step 603, the processing module 7 determines the maximum of the auto-convolution signal. Maximum of the auto-convolution signal is determined by locally fitting the auto-convolution signal by a second-order polynomial function, and then determining a maximum of the second-order polynomial function.

The coordinate of the maximum of the auto-convolution signal is considered as being twice the position of the bead along the third axis y.

As the interference pattern is periodic, the characteristic length of the interference pattern is not the half-length of the spot $\sigma$ (as in the first embodiment), but a fraction of the pitch of the fringe pattern (typically $\frac{1}{4}$ of the pitch, which is substantially inferior to $\sigma$).

In addition, computation of positions $x'_1$ and $x'_2$ of the centers of the spots along the axis x can be made by unidimensional averaging and unidimensional Fourier processing, which requires less computing resources than computing the radial bead profile in 2D involving nx·ny squareroot to be taken for all the pixels in the area nx ny around the bead.

Moreover, spreading of the spots along the axis x causes an increase of the number of pixels impacted by the light radiations, and therefore gives the possibility to dramatically increase the total number N of photons contained in each spot before saturation of the detector. As a result, the precision of the measurement is increased.

Each spot contains fringes which may be viewed as a periodic collection of spots, having a full width at half maximum of:

$$\sigma = \frac{i}{4}$$

$$i = \frac{\lambda}{2\sin\beta}$$

where i is the pitch between two successive the fringes, $\lambda$ is the wavelength emitted by the source and $\beta$ is the angle between two beams coming from a pair of slots.

The precision of the computation of the center of a spot is thus:

$$\frac{\lambda}{8\sqrt{N}\sin\beta}$$

where N is the total number of useful photons contained in the spot, each fringe contributing to the precision of the measurement with the number of photon contained therein.

The number N of useful photons is the total number of photons contained in the image which contribute to the interferometric pattern. The number N is:

$$N = N_0 \cdot c \cdot n_x \cdot n_y$$

where $N_0$ is the number of photons corresponding to the saturation threshold of one pixel of the detector (i.e. the well depth), c is the contrast of the fringes (quantifying the proportion of useful photons) and is comprised between 0 and 1, $n_x$ and $n_y$ are the number of pixels according to the axes x and y defining the extent of the spot.

Finally, the precision of the computed z coordinate of the bead from two spots is:

$$\frac{\lambda}{16\sqrt{N}\sin\beta\tan\alpha} = \frac{i}{8\sqrt{N}\tan\alpha}$$

This precision can be adjusted by controlling simple parameters, such as the object aperture angle (tan $\alpha$), the spatial frequency of the fringes (sin $\beta$) and the area of the spot which sets, for a given detector, the total number N of photons contributing to the measurement of the coordinate z of the bead.

Figure 16:
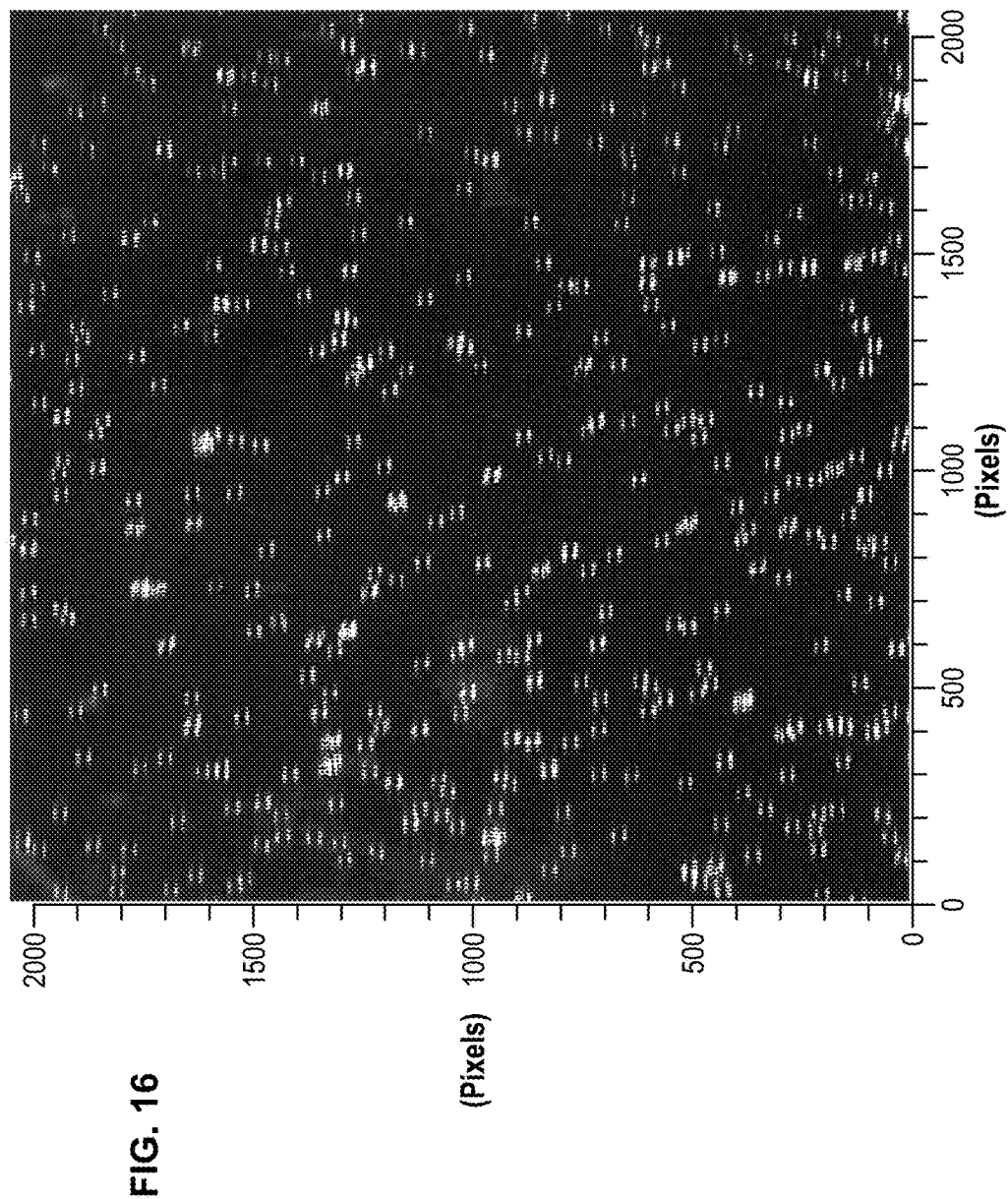
FIG. 16 shows an image generated by the detector for a batch of beads, obtained with the device of FIG. 15.

FIG. 16 shows an image generated by the detector 6 for a batch of beads.

The image has been obtained with a red LED centered around 660 nanometers and having a spectral width of 15 nanometers, a microscope objective having a magnification of 40, a 4F arrangement having a first lens having a focal length of 125 millimeters and a second lens having a focal length of 100 millimeters, a transmission mask having four slots and a separating arrangement comprising a tube lens having a focal length of 100 millimeters and two inclined glass blades arranged symmetrically around the axis x. Each bead was a paramagnetic bead having a diameter of 1 micrometer. The distance between the two pairs of slots was 2.5 millimeters, and the distance between two slots of a same pair of slots was 1.4 millimeters. Each slot had a width of 0.2 millimeters (along the axis x) and a length of 1.3 millimeters (along the axis y). The blades were inclined of +10° and −10° relative to the x, y plane. The thickness of each blade was 1 millimeter. The beads were placed in a microfluidic chamber substantially at the same position according to the axis z. The field of view was 400×400 micrometers. The image shows several pairs of spots, each pair of spots corresponding to one bead. Each spot contains an interference pattern made of parallel fringes.

The image can be scanned for determining for each successive pair of spots, coordinates of the corresponding magnetic bead.

The proposed solution does not necessitate a calibration phase for each bead. This greatly simplifies the measurements and eliminates the need for a high precision nanopositioning stage. The device and the method may be implemented with a standard microscope objective.

Figure 17:
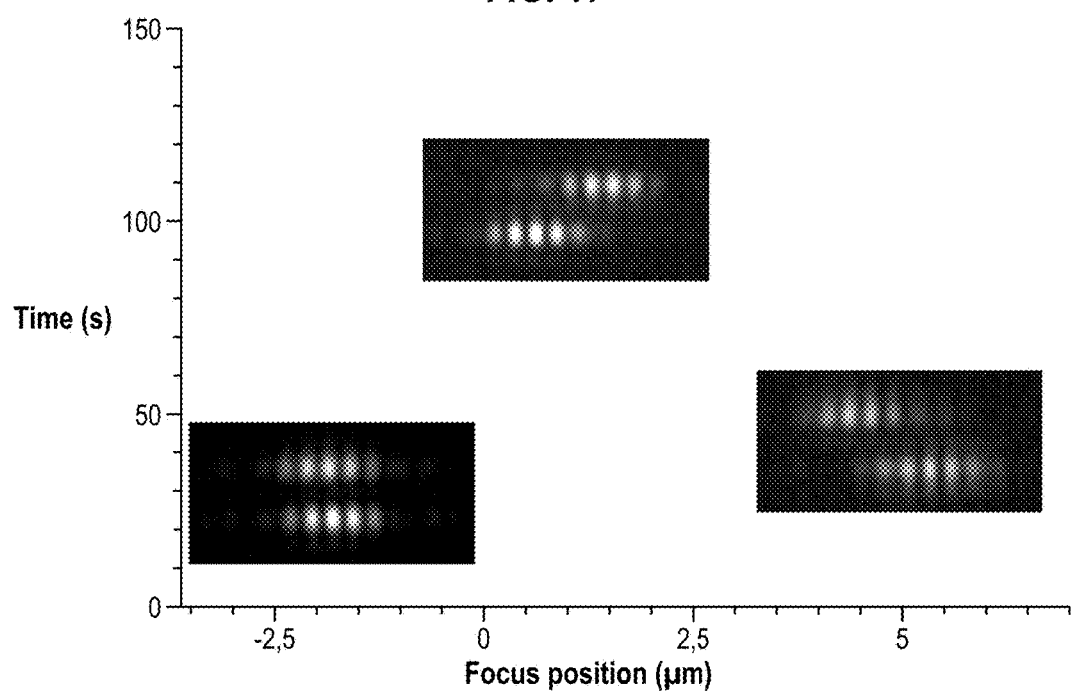
FIG. 17 is a diagram showing images generated by the detector when varying focusing of the optical objective.

FIG. 17 shows three images generated by the detector when varying focusing of the optical objective, The bead was stuck to the surface anchoring, while the optical objective focus position was moved as shown on FIG. 17. As can been seen on this figure, the focus position remained constant for 10 s, it was then decreased by 3 microns in steps of −0.1 microns for 30 s, the focus position was then increased to +3 microns in 60 steps lasting 60 s, and the focus was brought back to its position in 30 s.

Figure 18A:
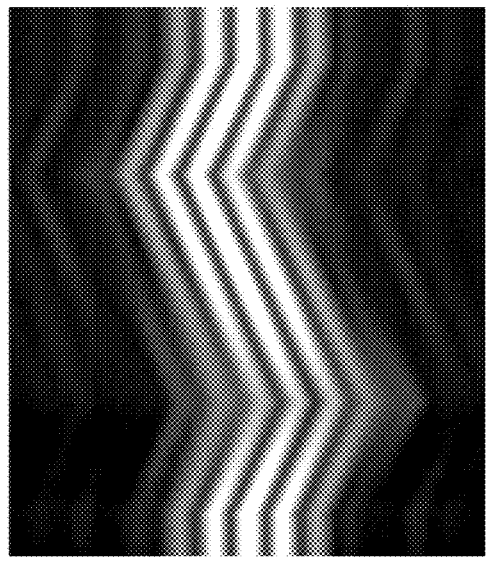
FIGS. 18A and 18B are diagrams showing variation of the position of the fringes of the first spot and of the second respectively.
Figure 18B:
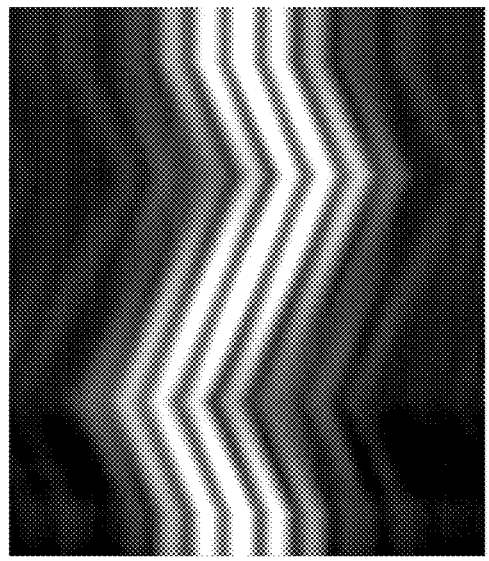

FIGS. 18A and 18B are diagrams showing variation of the position of the fringes of the first spot and of the second respectively.

The image intensity of each fringes system is shown versus time. Both are shifted along the axis x when the focus position moves but their displacement are opposite in direction. Each line of the diagrams corresponds to the averaging of one of the fringe system over typically 10 camera lines. These 1D profiles correspond to the signal that will be used at each frame to measure the bead position along the axes x and z.

FIGS. 19A and 19B are diagrams showing different signals generated by the processing module when processing the images of the first spot (FIG. 19A) and of the second spot (FIG. 19B).

For each spot, the first signal (at the top) is a Fourier transform of the averaged interference profile of the spot.

The second signal (in the middle) is obtained by bandpass filtering the first signal.

The third signal (at the bottom) is the phase signal of the second signal.

As can be seen in the insert of FIG. 19A, the Fourier spectrum of these profiles display a well defined peak (corresponding here to a mode number of 13). The bandpass filter is centered on this maximum and its width is adjusted to allow just the peak to be keep only. The result of this filter is shown in full line together with the second signal. By using the Hilbert transform, the imaginary part (dashed lines) associated also to the band-filtered signal is obtained. Having a complex signal is very convenient to measure the amplitude of the signal (in full line) and particularly to measure its phase. The filtered profiles have a clear maximum that moves along x with the change of focus position in z. This amplitude maximum is marked by the vertical arrow. The third signal shows the phase profile.

The phase signal varies linearly with x, its slope being related to the spatial frequency of the fringes. The position where the phase is equal to zero for the signal in the place where the amplitude is maximum defines $x(\varphi=0)$ which characterizes the fringes position, is marked by a vertical arrow. The phase is multiply defines (modulo $2\pi$) but the exact phase may be recovered either by continuity or by using the position of the amplitude maximum as a coarse value.

FIGS. 20A and 20B are diagrams showing the position of the fringes pattern measured using the phase signal (diamonds full lines) or the maximum of amplitude (circle dash lines) for the first spot and for the second spot respectively.

It is to be noted that the amplitude signal is roughly linear but presents some irregularities while the phase signal is extremely linear with minimal noise. Owing to small dissymmetry in the position of the slots in the amplitude mask, the slope of the two phase lines are slightly different.

FIG. 21A is a diagram showing an error signal: that is the value of the signal minus the mean value of each step (the signal has not been reported when the focus position was moving). On FIG. 21B, this error signal in x has been converted in a z signal. The z signal has a Gaussian distribution with a $\sigma$ of 1 nm.

Figure 22:
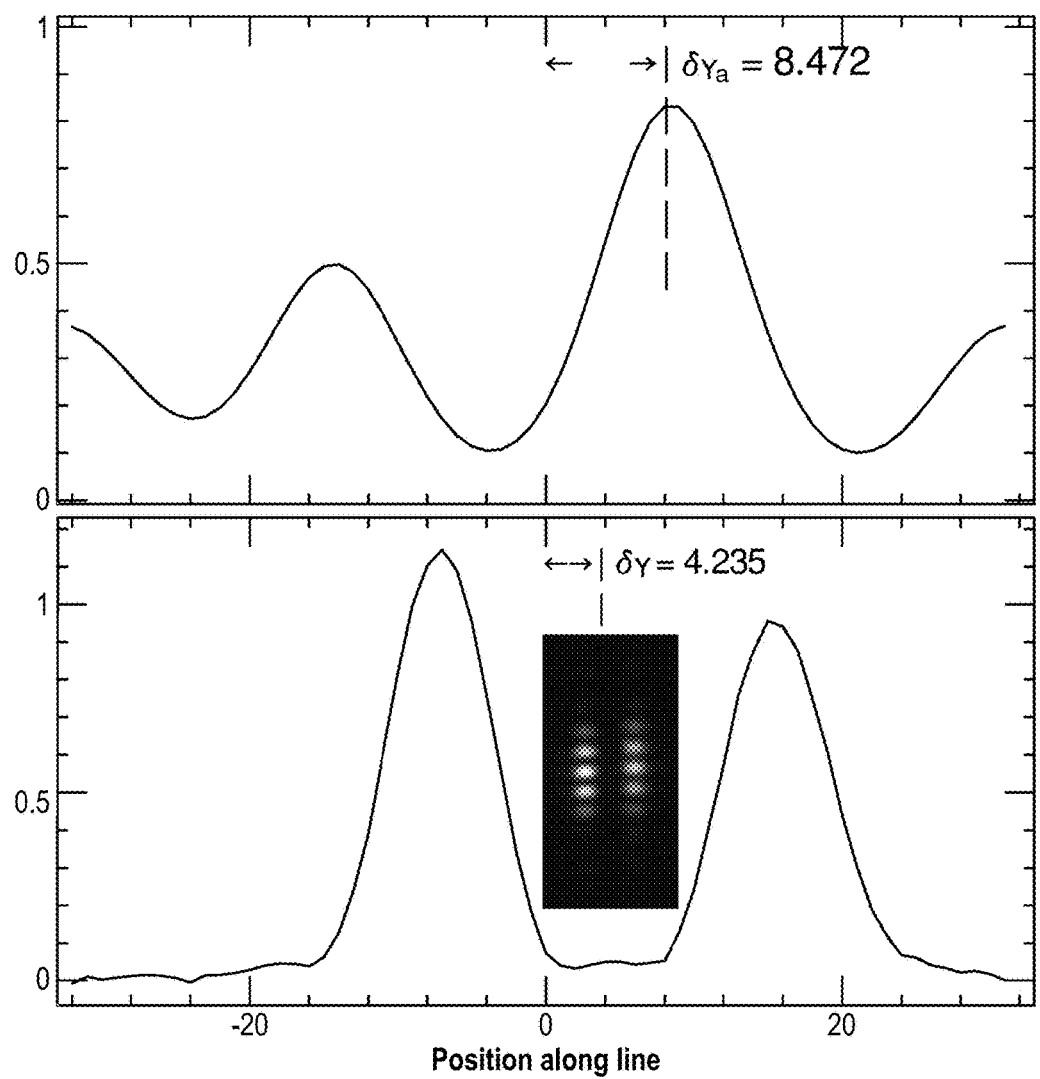
FIG. 22 shows two signals allowing to determine a position of a bead along the second axis x: the bottom signal corresponds to a mean profile of two fringes patterns, and the top signal is obtained by auto-convolution of the bottom signal.

FIG. 22 shows two signals. The bottom signal corresponds to the mean profile over 64 points of two fringes pattern, each peak corresponding to a fringe pattern. These two peaks are shifted on the right by a little more than 4 pixels. The top signal is the auto-convolution of the bottom signal, it presents three maxima with the strongest shifted by more than 8 pixels. Finding the position of the auto-convolution maximum provides twice the shift of the bottom signal. This allows tracking the position of the bead according to the second axis x (which is perpendicular to the direction of the fringes).

The invention claimed is:

1. An optical device for measuring the position of an object along a first axis, the object being subjected to light radiations emitted by a light source, the optical device comprising:
    an optical imaging system comprising an objective for collecting light radiations diffused by the object, the objective having an optical axis extending parallel to the first axis,
    having at least a first aperture and a second aperture, the first aperture and second aperture being spaced from each other along a second axis, perpendicular to the first axis, the transmission mask being arranged so as to let a first part of the radiations and a second part of the radiations which are diffused by the object pass through the first aperture and the second aperture respectively, while blocking a part of the radiations emitted by the light source which is not diffused by the object,
    a separating arrangement for separating the first part of the radiations from the second part of the radiations in opposite directions along a third axis, perpendicular to the first and second axes, and
    a detector having a detector plane, the detector being adapted for generating an image including a first spot and a second spot, the first spot and the second spot being representative of the separated first part and second part of the radiations impacting the detector plane,
    wherein variation of the position of the object relative to the object plane of the optical imaging system along the first axis causes variation of a position of the first spot and of the second spot relative to each other along the second axis.

2. The optical device according to claim 1, wherein the first aperture and the second aperture are arranged symmetrically on opposite sides of the first axis.

3. The optical device according to claim 1, comprising a processing module for processing the image generated by the detector, the processing module being configured for:
    determining a position of a center of the first spot in the image,
    determining a position of a center of the second spot in the image, and
    computing the position of the object along the first axis as a function of the position of the center of the first spot and of the position of the center of the second spot.

4. The optical device according to claim 3, wherein the processing module is configured for determining the position of the center of each spot by computing a maximum of the auto-convolution of an average profile of the spot.

5. The optical device according to claim 3, wherein the processing module is configured for determining the position of the object along the second axis and/or along the third axis from positions of the spots on the image.

6. The optical device according to claim 1, wherein the transmission mask comprises a first pair of apertures dividing the first part of the radiations into two first beams, and a second pair of apertures dividing the second part of the radiations into two second beams, and wherein the two first beams interfere with each other so as to create a first interference pattern within the first spot and the two second beams interfere with each other so as to create a second interference pattern within the second spot.

7. The optical device according to claim 6, comprising a processing module for processing the image generated by the detector, the processing module being configured for determining a spatial phase shift between the first interference pattern and the second interference pattern along the second axis, and for determining a position of the object along the first axis as a function of said spatial phase shift.

8. The optical device according to claim 7, wherein determination of the spatial phase shift comprises:
    generating a first signature signal representative of a spatial variation of the intensity of the first spot along the second axis,
    generating a second signature signal representative of a spatial variation of the intensity of the second spot along the second axis, and
    determining a first reference point of the first signature signal where a phase of the first signature signal is null near a maximum of an amplitude of the first signature signal,
    determining a second reference point of the second signature signal where a phase of the second signature signal is null near a maximum of an amplitude of the second signature signal,
    computing the spatial phase shift between the first interference pattern and the second interference pattern as the distance along the second axis between the first point and the second point.

9. The optical device according to claim 8, wherein the processing module is configured for determining the position of the object along the second axis from the first reference point and the second reference point.

10. The optical device according to claim 6, wherein the processing module is configured for determining the position of the object along the third axis, determination of the position of the object along the third axis comprising:

generating a third signature signal representative of a spatial variation of the intensity of the first spot and of the second spot along the third axis, computing an auto-convolution signal by auto-convolution of the third signature signal, determining a maximum of the auto-convolution signal, the coordinate of the maximum of the auto-convolution signal along the third axis being considered as being twice the position of the bead along the third axis.

11. The optical device according to claim 6, comprising a first light source arranged to emit light radiations toward the object according to a first angle and a second light source arranged to emit light radiations toward the object according to a second angle.

12. The optical device according to claim 11, wherein the first light source and the first pair of apertures are arranged such that a part of the light radiations emitted by the first light source and diffused by the object passes through the first pair of apertures while a part of the light radiations emitted by the first light source but which is not diffused by the object is blocked by the transmission mask.

13. The optical device according to claim 11, wherein the second light source and the second pair of apertures are arranged such that a part of the light radiations which is emitted by the second light source and diffused by the object passes through the second pair of apertures while a part of the light radiations emitted by the second light source and which is not diffused by the object is blocked by the transmission mask.

14. The optical device according to claim 1, wherein the light source is a light source with a short length of coherence, such as a light emitting diode (LED).

15. The optical device according to claim 1, wherein the separating arrangement comprises at least one blade having a face which is inclined relative to a plane perpendicular to the first axis, so that the first part or the second part of the light radiations which goes through the blade is translated along the third axis.

16. The optical device according to claim 1, wherein the separating arrangement comprises at least one prism having a face which is inclined relative to a plane perpendicular to the first axis, so that the first part or the second part of the light radiations which goes through the prism is deviated along the third axis.

17. The optical device according to claim 1, wherein the transmission mask is located in a Fourier plane of the imaging system or in a plane which is an image of the Fourier plane of the imaging system through an optical relay, so as to select parts of the light radiations which have been diffused by the object according to predetermined angles.

18. Method for measuring a position along a first axis of an object being subjected to light radiations emitted by a light source, wherein the method comprises steps of:

collecting light radiations diffused by the object by means of an objective of an optical imaging system, the objective having an optical axis extending parallel to the first axis, arranging a transmission mask having at least a first aperture and a second aperture so as to let a first part of the radiations and a second part of the radiations which are diffused by the object pass through the first aperture and the second aperture respectively, while blocking a part of the radiations emitted by the light source which is not diffused by the object, wherein the first aperture and second aperture are spaced from each other along a second axis perpendicular to the first axis, separating the first part of the radiations from the second part of the radiations in opposite directions along a third axis perpendicular to the first and second axes, and generating, by means of a detector having a detector plane, an image including a first spot and a second spot, the first spot and the second spot being representative of the separated first part and second part of the radiations impacting the detector plane, wherein variation of a position of the object relative to an object plane of the optical imaging system along the first axis causes variation of a position of the first spot and of the second spot relative to each other along the second axis.

19. Method according to claim 18, wherein the object is a magnetic bead.

20. Method according to claim 19, wherein a molecule having two ends is attached at one end to an anchoring surface and at the other end to the magnetic bead, the device being positioned relative to the anchoring surface so as to measure a distance between the magnetic bead and the anchoring surface.

21. Method according to claim 20, wherein a plurality of molecules are attached, each molecule being attached at one end to the anchoring surface and at the other end to an associated magnetic bead, the method comprising a step of generating an image showing a plurality of pairs of spots, each pair of spots being generated by one of the magnetic beads, and scanning the image for determining for each successive pair of spots, a distance between the magnetic bead and the anchoring surface.

* * * * *